US009017736B2

(12) United States Patent
De La Llata Romero

(10) Patent No.: US 9,017,736 B2
(45) Date of Patent: Apr. 28, 2015

(54) **METHOD OF TRANSFORMING INTO GENIN AND SAPOGENINS OF PARTICULAR PLANT SPECIES OF THE FAMILY *SAPOTACEAE* WITH THE USE OF EXOGENOUS ÃŸ-GLYCOSIDASES FOR THE PREPARATION OF COSMETICS AND DERMATOLOGICAL COMPOSITIONS**

(76) Inventor: Luis De La Llata Romero, U. Hab. Villa Olimpica (MX)

( * ) Notice: Subject to any disclaimer, the term of this patent is extended or adjusted under 35 U.S.C. 154(b) by 2101 days.

(21) Appl. No.: 11/632,961

(22) PCT Filed: Jul. 21, 2004

(86) PCT No.: PCT/MX2004/000052
§ 371 (c)(1),
(2), (4) Date: Jun. 24, 2008

(87) PCT Pub. No.: WO2006/009418
PCT Pub. Date: Jan. 26, 2006

(65) Prior Publication Data
US 2008/0261291 A1    Oct. 23, 2008

(51) Int. Cl.
| | |
|---|---|
| *A61K 36/00* | (2006.01) |
| *A61K 36/185* | (2006.01) |
| *A61K 8/97* | (2006.01) |
| *A61Q 5/00* | (2006.01) |
| *A61Q 7/00* | (2006.01) |
| *A61Q 19/00* | (2006.01) |
| *A61Q 19/08* | (2006.01) |

(52) U.S. Cl.
CPC ............... *A61K 36/185* (2013.01); *A61K 8/97* (2013.01); *A61Q 5/00* (2013.01); *A61Q 7/00* (2013.01); *A61Q 19/00* (2013.01); *A61Q 19/08* (2013.01)

(58) Field of Classification Search
None
See application file for complete search history.

(56) References Cited

U.S. PATENT DOCUMENTS

| 3,449,760 A | 6/1969 | Hardman | |
|---|---|---|---|
| 5,736,385 A | * 4/1998 | Tamura | ........................ 435/280 |

FOREIGN PATENT DOCUMENTS

| GB | 1510790 | | 5/1978 |
|---|---|---|---|
| GB | 1510790 A | * | 5/1978 |
| WO | WO 2004002504 | | 1/2004 |

OTHER PUBLICATIONS

Enjolfsson, Constitution and stereochemistry of lucumin, a cyanogenic glycoside from Lucuma mammosa Gaertn, Acta Chemica Scandinavica, 1971; 25: 1898-1900.*
Tuncel et al, Degradation of cyanogenic glycosides of bitter apricot seeds (*Prunus armeniaca*) by endogenous and added enzymes as affected by heat treatments and particle size, Food chemistry, Sep. 1998. vol. 63, No. 1. p. 65-69.*
Takeda et al, Constitution of lucumin and its related glycosides from Calocarpum sapota Merrill, Chem. Pharm. Bull 45 (4) 697-699, 1997.*
Lalitha et al, Isolation and properties of Saponins from *Madhuca butyracea* seeds, J. Agric Food Chem. 1997, 35, 744-748.*
Mohamed et al, Physical, morphological and chemical characteristics, oil recovery and fatty acid composition of *Balanites aegyptiaca* Del. kernels, Plant foods for human nutrition (Dordrecht, Netherlands), (2002 Spring) vol. 57, No. 2, pp. 179-189.*
Merfort, Phytochemical study of Lucuma mammosa, Inverni & Della Beffa S. p. A. Milano: 1984; 55 (5): 316-317.*
Takeda, T. et al. "Constitution of Lucumin and its related glycosides from Calocarpum sapota Merrill". Chem. Pharm. Bull, 1997. vol. 45, No. 4, pp. 697-699.
Bachstez, M. et al. "Notas sobre Drogas, Plantas γ Alimentos Mejicanos. X. Estudio de la Lucumina, glucosido cianogenetico del mamey (Lucuma mammosa G.)". Ciencia, 1948. vol. 9, pp. 200-2002.
Eyjolfsson, R. "Constitution and stereochemistry of Lucumin, a cyanogenic glycoside from Lucuma mammosa Gaertn". Acta Chemica Scandinavica, (1947-1973) 1971. vol. 25, No. 5, pp. 1898-1900.
Yeog, H.-H. et al "Some properties of beta -glucosidases from tropical plant species". Phytochemistry, 1994. vol. 35, No. 6, pp. 1391-.

* cited by examiner

*Primary Examiner* — Qiuwen Mi
(74) *Attorney, Agent, or Firm* — Welsh Flaxman & Gitler LLC

(57) ABSTRACT

Nontoxic aglycones of a particular species of the family Sapotaceae are obtained for preparing cosmetics and pharmaceutical dermatological compositions. These aglycones are prepared with the use of coarse raw kernel, or by a plurality of kernel products as raw material that contain the biochemical substrates, namely related glycosides to the lucumin. The transformation products consist of benzaldehyde, the main constituent of the genin recovery, and mandelic acid and mandelamide, the main constituents of the sapogenins. The process for transformation into genin and sapogenins includes the use of exogenous β-glycosidases other than from the family Sapotaceae as the biochemical transformation method into the respective enzymatic hydrolysis aglycones products, the genin plus sapogenins as obtained and after separation into the individual aglycones.

15 Claims, No Drawings

METHOD OF TRANSFORMING INTO GENIN AND SAPOGENINS OF PARTICULAR PLANT SPECIES OF THE FAMILY *SAPOTACEAE* WITH THE USE OF EXOGENOUS ÃŸ-GLYCOSIDASES FOR THE PREPARATION OF COSMETICS AND DERMATOLOGICAL COMPOSITIONS

BACKGROUND OF THE INVENTION

This invention relates to the obtaining of the cyanogenic glycoside, the lucumin and of the related glycosides structurally similar to the first, the lucuminic acid and the lucuminamide and its hydrolytic transformations to alpha hydroxylated derivatives, the first one initially with hydroxynitrile characteristic, as the mandelonitrile, later on turning to benzaldehyde, as finally obtained; the other two related glycosides are gotten and as well transformed; the second as carboxylic acid, similar to the mandelic acid, and the third in the amide of the same last acid; both last ones hydroxylated as finally accomplished, all of the three achieved and converted primarily in an extract together of genin and sapogenins respectively that are separated by their physical properties. These are derived by chemical or enzymatic hydrolysis of the related glycosides structurally similar to the lucumin, mainly of the genus *Calocarpum, Chrysophyllum* and *Lucuma* of the family Sapotaceae, all of them with biological activities. The biological activities show up as isolated compounds or in a mixture of extractive glycosidic substances, or as hydrolytic aglycones (glycosides lacking the "sugar" moiety) extracts of the previous ones; the two groups of derived aglycones the genin and sapogenins, isolated and purified with own chemical and biological characteristics of utility in consumption products, as presented in this work and the employment forms in cosmetics and pharmaceutical dermatological compositions and as the same in substitutes uses, as exposed here in.

The sources to obtain the hydrolytic derived aglycones, last so only in chemical structure, to the glycosides, but not unavoidably in the obtaining chain, here called derived genin and sapogenins, can be several principles or tissues of the trees of the family Sapotaceae (*Calocarpum sapota, C. viride, Lucuma mammosa, L. salicifolia* and of some other fruit-bearing trees of the same family known as "sapotes" included *Chrysophyllum*), as the barks, the leaves, the flowers or the sap; but as a renewable resource it results to be the kernel tissue used in several ways, from the whole rough, crushed or milled matter; or of what is left of the kernel as solid remainder after the lipidic expression or what is left as solid residue after the lipidic extraction (for the obtaining of the oils) or for some special circumstances it is also possible to obtain the aglycones from the related glycosidic extract. These last obtaining, for their accomplishment, is possible but not in a dependent mandatory way; the only thing needed are the kernels-bearing principles, contain them as it is in a natural way, without having suffered contact with polar liquids that extract these resources; and in this way it can be proceed to the aglyconic hydrolysis, from the kernel-bearing principles; like of what is left of solid residual products of both of the lipidic expression or the extraction or of the rough kernel matter, in whole, pieces, crushed or milled.

Of the raw materials mentioned in the previous paragraph, (resources to obtain of the derived aglycones), mainly of the kernels in rough state plainly milled or crushed or cut in small pieces or those used or of some preparation of them (kernels), for the obtaining of the derived hydrolytic aglycones (originated by the glycosides structurally related to the cyanoglycoside) of the related genus.

It can also be branched of in the previous kernel-bearing aglyconic obtaining and to achieve in an isolated extract or semi-purificated state the direct substrates of the "aglyconic" hydrolysis (enzymatic hydrolysis), and obtaining the related glycosides, without trash material, and once extracted later on to continue with the related hydrolysis or it is possible to obtain the related glycosides for other uses and being employed in the manufacture of elaborated products in extract or in isolated form for topical use.

The related glycosides to the cyanoglycoside preferably are used as "enzymatic" substrates to which are practiced a hydrolysis (being able to be chemical with organic or inorganic acids), to obtain the derived hydrolytic aglycones, the genin and the sapogenins initially mentioned. More over, this form of derivation to arrive to the aglycones does not have mandatory dependence in the obtaining chain, starting from this derived related glycoside (to the cyanoglycoside) in an extract concentrate or in isolated forms.

Practically in this work, the genin and sapogenins are obtained directly from the several preparations of the kernels, previously mentioned, without stopping in the glycosides obtaining branch off; obtaining to the stage of related glycosidic extract or in an isolated form, for then to derived in the aglycones. The kernel-bearing principles for deriving to the aglycones, this with the content of related glycosides in the kernel's matter preparations, makes possible the practicing of them, the extraction of the related glycosidic and the subsequent hydrolysis and in this way to obtain the aglycones; or it is also possible straying directly in the same course of the hydrolytic transformation to the aglycones, starting from the kernel preparations; or branching of to obtain to the related glycosidic compounds or in form of an extract (to the cyanoglycoside), obtained as a whole glycosidic extract, starting from the kernel preparations and these being used in the manufacture of cosmetic and dermatological compositions. These glycosides are obtained as a related glycosidic extract to the cyanoglycoside, or these glycosides can be isolated and in this way be used in formulations; or it is also possible for later to be re-taken the obtaining of the derived hydrolytic aglycones, but instead of using some preparation of the kernels, by the use of the prepared related glycosides, practicing them the hydrolysis, in a whole glycosidic extract form, conformed by the three related glycosides; or practicing them the same hydrolysis reaction in isolated form.

The extraction techniques and the isolation procedure of the cyanogenic and related glycosides for the obtaining of the derived hydrolytic aglycones are additionally more expensive in relation to the technique that starts of the different preparations of the kernels, via the direct hydrolysis to the aglycones; by these previously mentioned treatments of these products or preparations of the kernels containing the hydrolytic substrates related glycosides, to arrive to the derived aglycone without branching off to the extraction and the isolation of the related glycosidic compounds, straying directly to the derived hydrolytic aglycones; but both coming from the same previous, prepared material resources of the kernels of the related genus, but by different ways for their obtaining.

The preference for the obtaining of the cyanogenic and related glycosides is received by the remainders of the degreased kernels; this is because its eliminated and avoided some or the entire presences of the lipids in the kernels preparation, that interfere in the more expedite purification to these related glycosides.

Also the preference for the obtaining of the derived aglycones, the extracts of genin and of sapogenins, is received by the remainders of the degreased kernels, this is the solids residual of the kernels after the lipidic expression and afterward/or by degreased solid residue of the lipidic extraction, without being restrictive the raw material that is started in this obtaining, but being of more affords because of the advantage of the preceding profit uses of the obtaining of fixed lipids that are recovered of the kernels previously.

The genin and sapogenins extracts biologically active are obtained starting from the lucumin, the cyanogenic glycoside and of the related glycosides, the lucuminic acid and the lucuminamide; "vegetables secondary metabolites" of the related genus that mainly transformed biochemically, with added enzymes of different genus (exogenous, extrageneric), adequate, appropriate and particular for the way of taking place and for their capacity to due the reactions of aglyconic hydrolytic division, processes that are achieved with the detoxificación of the lucumin (freeing from the cyanide radical), in the genin extract blended with the extract of the sapogenins that is achieved by the same and similar transformation of the other remaining related glycosides. The lucuminic acid and the lucuminamide of the "sapotes" are achieved by the previous transformation in the derived alpha hydroxylated compounds, connected to a benzylic ring (phenylic); one is gotten as a carboxylic acid, like the mandelic acid, and the other one as the amide of the derived same previous acid; as obtained in the sapogenins extract; and by another side, the obtaining of the genin derived benzaldehydic extract, as previously mentioned with similar chemical characteristic to the other two aglycones. However, both the genin and sapogenins extracts, are obtained united in a mixture of extracts, this is if having started of some preparation of the complete kernels-bearing principles, with the whole content of natural integer of cyanogenic and related glycosides.

The three aglycones mentioned above are acquired by the hydrolytic reaction of break up of the "sugar moieties" from the parent related glycosides.

The obtaining of the solid residual product of the lipidic expression here also named as "the expression crackling", or the solid residual (remainder) product of the obtaining of the fixed total lipids; and by the other hand the obtaining of the solid (remainder) residual product of the lipidic extraction, as the same here named as "the degreased flour" or the solid residual product of the lipidic extraction, both as vegetable remainders of the "sapotes" kernels that stay as solid residual of those processes of obtaining of the lipids. This solid residual which serve as products and raw materials, respectively, for that and for this following process of this related applications, for the obtaining of the cyanogenic and related glycosides and to their derived genin and sapogenins, which are reasons of this application and of the precedent related application of patents in these processes by the same author; made up of products and raw materials that are also constituted as elaborated and initial matters respectively for this invention and the precedent.

The election technique for the obtaining of the genin and sapogenins extracts is the enzymatic hydrolysis and preferably the vegetable tissue of substrate is selected of the rough milled kernels or as a prepared of solid residuals of the presiding obtaining of the lipids, of degreasing for the obtaining of the fixed total lipids of expression and the solid residual of the lipidic extraction of these processes of the genus. *Calocarpum*, *Chrysophyllum* and *Lucuma*, without being restrictive for this hydrolytic obtaining the raw materials as the referred substrate of use, but being of more profitable afford in their rendition in the integral use of the kernels, as it was said previously, being able to be the same tissue of the fresh or dry rough milled kernels, or different prepared more elaborated kernels residues as those mentioned previously which are used.

The raw materials in particular of the kernels that are used mainly in the presently and precedent work are the milled kernels (seed lacking the endocarp), being able to be used rough, as such. If the product which is wanted to arrive are the derived hydrolytic aglycones it can be started of any raw material coming from the previously mentioned kernels, being able to be the rough kernels or of some preparation of the same lipid removed kernels, as the solid residuals of lipidic expression or of solid residual of lipidic extraction processes, without being practiced some extractive procedure or washes with polar solvent (as water).

As it was said previously to arrive to the derived hydrolytic aglycones it is also possible to start of the cyanogenic and related glycosidic extract, as a whole glycosides concentrate or as purified lipidic and isolated glycosides, and being able to practice the hydrolytic process afterwards. However, this last technique to arrive to these derived aglycones is relatively too expensive and without a strict dependence to be started of these glycosidic resources extracted and in a more elaborated isolated or purified form than that of the original kernels or the degreased kernel preparations. Of being required the cyanogenic and related glycosidic extract or some glycoside of these in isolated form it is the reason for which it would serve straying in the obtaining of the same ones. If its wants to arrive to the derived hydrolytic aglycone in a more economic form and in an easy and effective way, it serve for this the solids degreases residual products of the kernels (degreased by, expression or extraction), being equally feasible the isolation of the aglyconic hydrolysis products among these material resources or products obtained in the degreasing process, to the same conditions of simplicity The hydrolytic aglyconic derives products are possible to obtain by a practice of a chemical or enzymatic hydrolysis. Preferably, the enzymatic hydrolysis is use, practiced directly to the "expression crackling" and/or "degreased flours" of the kernels.

The hydrolytic derives which are the whole extracts of genin and sapogenins of the related "sapotes" are obtained by chemical or by the other improved enzymatic hydrolysis. It is also possible to use the related glycosidic extract as raw material in the hydrolytic attainment, as later described, which is in the kernels in gross form or to use the kernels in degreased total or partially forms or it can be started with the related glycosides in isolated forms as previously mentioned.

It is also possible to use the fresh kernels or dried milled ones, without degreasing, which are alternating raw material in variants of this invention, for the obtaining of the cyanogenic and related glycosides or to derive directly in to the chemical or enzymatic hydrolysis products.

The purpose of the present invention is to put these products with the referred principles of the cyanogenic and related glycosides or of its derived hydrolytic aglycone, the genin and the sapogenins plus, the whole group of fixed lipids of *Calocarpum*, *Chrysophyllum* or *Lucuma*, within reach of the public in general in an ingenieriles forms by means of industrial transformations of application, which solves the technical problems in the lipidic extraction, uses that don't taken in advantage these and continue the use of the rough matters in medicinal plant and in rustic traditional other uses, for modern practice in dermatology and cosmetology, nutrition or pharmaceuticals as in other utilities like substitutes employments of the same, in a more satisfactory way and of rational use of resources not well used in coarse treatments or without being used and leaf as vegetable matter of waste.

In remote regions of the center of Mexico and more to the south, vegetable matter of *Calocarpum*, *Chrysophyllum* or *Lucuma* are used as medicinal remedies, cosmetics and nutritious recipes in traditional uses, it employ preparations including to the kernels. The residuals of the kernels after the "solvent extraction" of the oils (that contains the cyanogenic and related glycosides principles as in this work said) are also reported with activity against painful affections of the skin, by mean of applications like cataplasms. The bark is reported bitter, used as astringent, and that it contains the lucumin, the cyanogenic glycoside. Decoctions of the bark are taken as pectoral's aids. In Costa Rica bark and leafs tea's are administered in arteriosclerosis and hypertension. The milky sap is emetic and anti-helminthic and it has been use topically for the removal of nuisances and of fungal skin growth.

They also take decoctions of the bark of the yellow sapote as febrifuge or in eruptions of the skin. The seed is prepared as remedy for cutaneous ulcerations.

In alternating variants of the present invention, there are also found in the seeds, triterpénicos, steroidal, and cyanogenic compound like as the alpha and beta amirin, the lupeol, lanosterols or of the lucumin, free or esterified.

These plants have a great variety of nutritious and medicinal traditional uses of which the main use is the fruit pulp for their excellent flavours and in traditional recipes of high content of proteins, carbohydrates, fibres, fatty, mineral salts, vitamins; specially carotenoid compound, thiamine, riboflavin, niacin, ascorbic acid.

The vegetable matter of *Calocarpum*, *Chrysophyllum* or *Lucuma* are also appreciated for their high content of fixed and volatile oils present and that they also have traditional uses in the foods and in homemade remedies for the use in the skin and the hair. However all these preparations of traditional use have not been totally developed because of technical impediments concerns in the separation and isolation methods of these active principles that give these effects and taken to industrial processes and of consumption.

The volatile oils in the traditional preparations are purely with an ethereal aroma contact effect of the vegetable rough matter, that is not possible to be separate of the vegetable matter in a conventional way and also a feasible way of being transformed and separated at the present time, as in the form explained in the obtaining of the same ones in the presently work. These essential aromas (volatile oil) characteristic of the related plants that are not attractive to be obtained by the conventional techniques to achieve these insoluble aroma materials here called the genin extract (a fraction), and another gotten as soluble water fraction the sapogenins extract, that are intimately bounded to the structural matter of the plant, in particular in the inside kernel, as it turn out to be the glycosidic sapogenic (froth making) matter.

The seed is reported to be source or substitute of the perfumery fragrance "Noyeau" and of alcoholic drinks, substituting the seeds of bitter almond by peach, "peach melocoton", apricot or "prisco, dry small peach" being the obtaining of the "sapote" kernels" in the present work different to the treatments of the previous reference.

In regions where the pulp fruit of the *Calocarpum*, *Chrysophyllum* or *Lucuma* is eaten copiously that is as nutritious matter thoroughly, that imperceptibly contains active ingredients for that of traditional estimates medicinal activities mentioned previously, is observed that these population conserves good conditions in their skin and the hair, attributable to the daily use or annual seasons consumption of this food. These active ingredients are also present in the rest of the plant and in the kernels, as it is said in the "popular voice".

The fruit of *Calocarpum*, *Chrysophyllum* and *Lucuma* have many uses in the traditional recipes and of economic considerable rate and the non consumable parts as food have diverse uses in cosmetic, nutritious and medicinal preparations of topical, local traditional rustic use, which don't end up separating the principles and identifying the particular effects in isolated form or to separate the toxic compounds and to enable some substances of the vegetable matter. The use of the cosmetic remedies and medicinal dermatological traditional homemade use, is not possible being used in a diffused form because aesthetics reasons and of appearance that are not able to isolate the active bound matter of the vegetable matter of support of the plant (or of structure or of trash in the kernels) that intervenes in the appearance in these prepared applications of traditional use and that they limit its daily and routine use which is the most beneficial way and of more results in its appliance. The same thing happens in nutritious traditional preparation uses, starting from the kernels, which are limited because the toxic content present, which the work here presented as patent application, due resolves, returning them innocuous.

The traditional knowledge confers to the oils of the common sapote, *Calocarpum sapota* or to *Lucuma mammosum* promoter activity of the growth of the hair, however studies in the University of California in LA (Los Angeles) (1970), by means of clinical tests practiced to the oils, fail in the detection, and do not find this activity, but they confirm that the oils of *Calocarpum sapota* are effective to stop the fall of the hair caused by seborrheic dermatitis. We found these same activities that is attributed traditionally to the "sapotes" of promoting the growth of the hair and that badly have been attributed isolate to the fraction of oils or the phosphatidic fraction or another oily fraction of the fixed total lipids portion by its self, because a scarce or not acting independently but having it in synergy with others derived of the seed like here revealed. The present invention has found this same activity in other extracts coming from the kernels (as the same last mentioned clinical oils studies) that due present the very defined activity on the hair follicle, of increasing its growth or of increasing the transformation of hairy hair to terminal hair by the stimulation with the mentioned extracts. This extracts comes from material derived of cyanogenic and similar related glycosides or that it remains in the solid remainder after the oils or the entire of the fixed lipids or some of these oily fractions have been obtained of the vegetable matter, or as said previously, with what remains as solid residues of lipidic expression or by the degreasing with non-polar solvent (lipidic extraction) or by the obtaining of oils in rustic traditional techniques. The solid residual that is left of the vegetable matter by the lipidic expression or the solid residual that's left by the lipidic extraction, that are chemically hydrolysable or mainly enzymatically. These activities are related about derives of the cyanogenic and related glycosides. This glycosides which are structurally similar, as that extract that contains the lucumin, and of the similar glycosidic compounds, the lucuminic acid and the lucuminamide. In the present invention these active compounds are obtained and then transformed in an exogenous enzymatical hydrolyzate, giving the active aglycone extracts previously mentioned, of genin and of sapogenins with the action of stimulation of the hair follicle and of other activities like mention previously and detailed in forward pages. To this extracts of derived aglycones that we will call here the sapogenins extract for coming from a hydrolyzed glycosides which is sapogenic (or froth forming) of the family Sapotaceae (a vegetable family classification) and of the related genus of a group of fruits called "sapotes". This extract can act in synergy with the volatile oils portion of the same plants coming from the kernels of the "sapotes" which are those who play these activities, the genin extract, a "ethereal" portion of lipids which here is also a matter of charge of claims in the present application. As the same as with the sapogenins extract or sapogenins their are also obtained in union with the genin extract that we will also indistinctly here call as genin (or the essential oil or volatile oleaginous fraction), both coming from the same cyanogenic and similar related glycosides of these present work of the "sapotes." The genin extract is constituted as the essential oils (or to some of the essences) of the "sapotes" that together with the sapogenins extract, both properly formed as one whole extract (when it is started from the whole or total form extract of the cyanogenic and related similar glycosides, or started of some preparation of the kernels) where it is obtained as a volatile material, aromatized fraction, of insoluble and soluble matter to the water of the "sapotes" with a well defined biological activity.

Of the preliminary tests, it has been known that of the cyanogenic glycosides and related structurally similar glycosides, which are contained in the rough kernels, is of where the genin and sapogenins come from. After being practiced the expressions and/or the non polar extractions, after being recovered or left apart, the liquid lipidic portion of both processes, these glycosides remain in the solid residues; from these solids is where the extracts of the genin and the extract of the sapogenins as aglycones of these glycosidic compounds are obtained. By means of a polar extraction processes practiced to the prepared or rough kernels these glycosides are recovered; and by the cleavage hydrolysis reaction of the "sugar" moiety" of these last ones, in the extract, or in isolated form, or from the rough kernel directly and then separated is able to obtain these principles, by these work. These aglyconic hydrolytic derives, existing in the support and nutrition germinal amyloidal structure of the kernels of the "sapotes" is what is obtained of importance. It has also been possible to know that the genin constitutes an oily odoriferous aromatized principle with the characteristic aroma of the vegetable matter in an isolated intense form and that in the topical application it is mainly an rubefacients agent and selective contrairritante for some epithelia like that of the face and the hairy scalp, that alone in the applied tissue it produces irritation of hyperaemia type, heat and pruritus and is of use in cosmetology and pharmaceutical dermatological compositions and with possibility in nutritious and alternating substitute uses.

The sapogenins in combination with the genin (both ones volatiles), together with the fixed oleaginous, not volatile fraction, which in preliminary tests have demonstrated to possess synergistic activity that is about an agent with topical defoliation activity, enhanced by the other lipidic, volatile and not volatile fractions of the same "sapote" kernel, with positive effects in the renovation and stimulation of the development of the epidermis included these effects to the hair follicle; also with activity like agent of percutaneous absorption for a watery continuous phase in union to a dispersed lipidic phases or in hydrated lipidic lamellar phases or as vesicles of the liposomal type that conform them or that contain them and their feasibility to pass to deep strata of the epidermis and with the variation of furthermore different, additional bacteriostatic and fungistatic effects which are also produced by the referred extract or as purified substances.

On the whole these substances or extracts, the genin and the sapogenins or in form of isolated compounds plus with their individual activities or in synergy with a fixed lipids fraction, being able these last ones also to be of the "sapotes", and of the cyanogenic and related structurally similar glycosides of *Calocarpum*, *Chrysophyllum* or *Lucuma* it is possible the industrial production of a wide range of cosmetics and of pharmaceutical products of topic use with the mentioned effects and facts with this finality, as the results of the present inventions, that are the extracts of genin and sapogenins which are also feasible being used respectively as flavouring agents and preservers against microbial growth in cosmetic and pharmaceutical compositions, in foods, like as in another alternating or substitutes uses of these extracts and derived presented here.

The objective in the matter of this invention is to make cosmetic and pharmaceutical dermatological preparations with properties of renovation of the epidermis and as promoters of the conservation of the hairy scalp and which are characterized for having substances of *Calocarpum*, *Chrysophyllum* or *Lucuma*, the "sapotes" as those derives of the cyanogenic and related similar glycosides, the genin and plus the sapogenins; extra by the fixed total lipids including the fixed oils, fosfolipidos (lecithins) and of non saponificable lipidic material as residuals of glycosidic triterpenic, steroidal or sterols, components of the not volatile total oleaginous fraction; and as by the same cyanogenic and related structurally similar glycosides; all with biological activity. The total fixed lipids of the "sapotes" (or the not volatile oleaginous whole fraction), with collateral or synergistic activity to the mentioned effects to the oily volatile, insoluble material; these seconds conformed by an aglycone, the genin, separated from the other derived aglycones, the sapogenins, also with volatile but soluble to the water characters respectively, that are obtained by the same and of their corresponding glycosides of where they come from and that these last ones are achieved in an extractive different processes and of their respective separations, all containing beneficial activities to minimum dose in the skin like the hydration plus the previously mentioned activities. The cyanogenic and related structurally similar glycosides of the "sapotes" appear apart from their biological activity, which are used mainly on the whole as hydrolysable substrates or in isolated or by their presence in extracts and prepared or in the treated kernels or as rough matter.

SUMMARY OF THE INVENTION

The cosmetic or pharmaceutical dermatological preparations according to the invention contain the active substances preferably as pure compounds forms or as semi-purificated essences, or as vegetable extracts or as hydrolytic products or as expression products all of them soluble and easily to manipulate and to deal and secure, without incompatibilities which these active ingredients contain. These include the mixture of cyanogenic structurally similar glycosides or in an isolated pure form; the genin and the sapogenins as two isolated extracts or each of these last ones in isolated compounds forms or in a mixture in union of sapogenins and genin. These active substances include the volatile oils, which constitutes part of the oleaginous components, of the "sapotes", in conjunction with the fixed oils that are constituted as a mixture of non volatile oils, together with another non volatile phosphatidic material as an oleaginous fixed fraction, more to another lipidic fraction of insaponificable material, as triterpénicos and esteroidales glycosidic residuals or of the "sterols", conforming the fixed total lipids, reasons of these. Because for these is why they are called the whole portion of, "total" fixed lipids, for being integrants, conforming of the sum of non-volatile lipids present in the kernel.

DETAILED DESCRIPTION OF THE INVENTION

It is known that the "sapotes" contains lucumin and their chemical structure has been elucidated, although it is not known, the enzymatic endogenous transformation, in the literature or in practices or in a natural way with its own enzymatic mechanisms of the kernels, of these same structurally similar glycosides, related to the cyanoglycoside; or further more by exogenous means (of organism or tissue outer development), from other genus (extrageneric) transformations, using enzymes of other generic vegetable or microbial, to the hydrolytic aglycone derives, as the genin with its benzaldehyde content or of the other aglycones coming of the other related glycosides, the lucuminic acid and the lucuminamide, transformed in similar conditions to the other sapogenins hydrolytic aglycones derives, as the hydroxyl-compounds with acid characteristic similar to the mandelic acid and to the amide of this last acid, from this group of glycosides of the "sapotes" of these genus, and their use in cosmetics and dermatological compositions with pharmacological activities.

By means of the chemical synthesis it is possible to arrive to the benzaldehyde and to the racemic mixture of the mandelic acid that are the nearest analogue compounds to the ones encountered in the extracts of the hydrolysis products of the cyanogenic and related glycosides of the vegetable matter coming from *Calocarpum, Chrysophyllum* and of *Lucuma*.

The cyanogenic glycosides as the amygdalin, the prunasin which would come to be the nearest more similar analogues to the lucumin (the existent cyanogenic glycoside in the "sapotes"), which are obtained mainly by extraction of vegetable matter of different genus like of *Prunus* of the species of the bitter almond, of the peach, of apricots, of cherries, of plum or prune etc.; or the racemic mixture can be synthesized chemically of similar analogues of the amygdalin, of the analysis of an undecided and finally rejected activity on the patent of these similar chemicals of the lucumin, and of those derives of the leatriles like that of Leatrile that is the synthetic derived "of the amygdalin or of the derived beta mandelonitrile glucoside or of the prunasin". The amygdalin and the prunasin are also attained of natural vegetable extractive origins as having said previously.

The extracts obtained with the cyanogenic and related structurally similar glycosides of the "sapotes", are used mainly in the present invention for the obtaining of the deglycosilated, desnitrilated, detoxificated hydrolytic derived as the genin, derived of the lucumin; the other two related similar glycosides are also obtained deglycosilated as the sapogenins.

In the case of the "sapotes" the hydrolytic extracts obtained starting from the cyanogenic glycoside present in the vegetable matter, that is the benzaldehydic derived in the genin extract; and others from the lucuminamide and lucuminic acid, there are obtained a carboxylic acid and a amidic derives with a hydroxylated similar character to that of the mandelic acid (and as mandelamide respectively). The sapogenins is enriched by different component substances of the extract that are obtained of the vegetable matter of the "sapotes" and besides by not using energetic, forceful, rebellious chemicals reagents in their obtaining or in their separation and by the use of minimal extractive material in the obtaining, as a concentrates, of these derived aglycones as hydrolysis products, by chemical or mainly enzymatic hydrolysis. These two, genin and sapogenins aglycones extracts, are obtained as a united group of substances in a whole extractive, which is characterized by the same equivalent process of obtaining and for their biological activities and for their chemical properties of biological origin, as an ulterior independents genin extract and sapogenins extract, with a minimum cost and work impulses in their obtaining, compared with the synthetic process that requires of expensive chemical reagents, of onerous production equipments and costly purification techniques and the most important thing that one obtains products with different chemical and biological properties, with varied pharmacological activities.

The same thing happens in the extractive process starting from the previous mentioned vegetables different from the "sapotes", like for example in the amygdalin processes of hydrolysis and that of the prunasin to give benzaldehydic compound. These processes starting from the previously mentioned vegetables different from the related "sapotes", however they suffer in difference with the methods reasons of the present invention, that these forms of deriving don't define methods, by enzymatic exogenous extrageneric hydrolysis mainly as in the present invention to the derived benzaldehydic and the hydroxylcompounds (ref. 39) as the acid and their amide starting from the group of related glycosides to the lucumin of the "sapotes." In contrast the lucumin and its related similar glycosides, of the "sapotes" by the referred techniques in the present invention in whose obtaining methods and uses as the aglyconic enzymatic hydrolyzates which uses exogenous (of outer organism development), extrageneric (coming from other genus), zymogens (generator of enzymatic activity) to obtain the derived benzaldehydic genin extract and also to achieve hydroxylcompounds, with benzyl-α-hydroxylated carboxylic acid characteristics, similar to the mandelic acid and of its amide (the mandelamide), or as the sapogenins extract and their use in cosmetics and pharmaceutical dermatological compositions, being all of these objects of the present invention.

With this hydrolytic process practiced to the lucumin and to its related structurally similar glycosides of the "sapotes" but mainly with the process of enzymatic exogenous extrageneric hydrolysis, their are obtained characteristic extracts with different substances that are obtained by these same, described later on, obtaining process and of separation, constituting the organic volatile matter of the "sapotes" coming from the cyanogenic and the related glycosidic portion (in the rough content of the kernels, or in isolated form, or as a whole glycosidic extract, constituted by the three related glycosides). The hydrolytic products are the genin or the genin extract (or the volatile oils or essential oils or to the essence of the "sapotes") and on the whole constituted by other obtained volatile organic substances and carried out in the same separation process, insoluble and soluble to the water respectively, starting from the vegetable matter of the "sapotes." The constituents of the sapogenins extract, both with hydroxylated character, one acid and another with amidic characteristics, as is defined later on. These genin and the sapogenins extracts are constituted as the products of enzymatic, exogenous, extrageneric hydrolysis, of the cyanogenic and related structurally similar glycosides of the "sapotes." The sapogenins has feasibility of being crystallized as two hydroxylcompounds, both with carbonyl characteristics one as a carboxylic acid and another as an amidic derivative (of these same previous acid); as for the same the benzaldehyde of the "sapotes" is obtained in form of an isolated extract.

It is described in the literature that it is obtained benzaldehyde by chemical synthesis and it is obtained with contamination of chlorine or by products of oxidation of the toluene in differences with the genin of the "sapotes" that are characterized by the peculiar scent to the related plants and that it is obtained without contamination of chemical reagents as the benzal chloride used in the chemical synthesis or by made ups of toluene oxidation in other forms of synthesizing it.

The benzaldehyde also occurred in some other kernels as those mentioned previously different to the related "sapotes", that contain amygdalin, as that of the bitter almond, also well known as *Prunus amygdalus*. In these bitter almond their exists its own enzymes of endogenous mechanism functions (own internal, of their same glycosidic metabolism, or glucosidases systems) are found in the seed of this genus, that catalyze the hydrolysis of the susceptible glycosides in these tissues of the vegetable matter, as that of the kernels of the mentioned almond, called trivially "emulsins" (glucosidases); when the kernel is crushed and then it enters in contact with the glycosidic substrate present in the same "milled" tissues, by breaking the endogenous cytoplasmic compartments of the sub-cellular or extra-cellular tissue which contain them, and the hydrolysis of the present glycosides takes place in the presence of cytosol (or water), and react giving benzaldehyde or the essential oils of the bitter almonds. These essential oils of the bitter almond are organoleptical different and with some other characteristics differences to the essential oil of the related "sapotes", which it also contains benzaldehyde but in bounded form and with out active or functional glucosidases; besides obtained with a series of particular compounds that are accompanied in the extract that characterizes the essential peculiar oil, belonging to the volatile oils of the related vegetables, to the "sapotes", with their characteristic aroma of where they proceed, being able to embrace different forms, from hydrocarbons (terpenes and sesquiterpenes), alcohols, acids, esters, aldehydes, ketones, phenols and or lactones with different odoriferous volatile characteristic of the same plant and that distinguish them of other genus, as from those mentioned different to the "sapotes" in the similar extract.

It is known that of the genus *Prunus amygdalus*, the bitter almond it is obtained the benzaldehyde, this is because in the seed of this vegetable their exists (endogenous) enzymes, amygdalase, glucosidases peculiar, specific of this genus of plants which hydrolyzes their own amygdalinic glycosides. In the genus *Calocarpum, Chrysophyllum* and *Lucuma* the glycosides exists especially the lucumin (the cyanoglycoside) and also by the related similar glycosides to this last one, which are very similar in chemical structure to the amygdalinic glycosides genus, but which vary in their disposition and concentration and in its "residual sugar" moiety of these glycosides. (The related glycosides to the amygdalin corresponding to the *Prunus* genus are the amygdalic acid [or amygdalinic acid] and the amygdalamide respectively; these are not known if they come from natural or artefact origin). The "sugar" in the amygdalin is gentobiose, for primaverose in the lucumin of the "sapotes" and also in their related similar glycosides, but that in the aglycone moiety are similar among them; but it exists as main differences the concentration, disposition and of the inability in the genus *Calocarpum, Chrysophyllum* and in *Lucuma* to hydrolyze its related glycosides in a homogenized integrated exclusively by their own seed endogenous enzymatic mechanism of glucosidases to the corresponding aglycone. This last homogenized is integrated in by its own (endogenous) existent substrate-zymogen of the same seed and reacting independently and individually; in the case of the "sapotes" this event does not happens and it is not transformed by their own biological, same typical catalytic enzymatic systems of degradation, with no internal function and the glycosides not being modified to the genin and sapogenins (in the state of non germinal seed); but with these technical manipulation, here presented, with the introduction of an external exogenous zymogen, that can carry out the not effected reaction, of "aglyconic" hydrolysis in the "sapotes" (carried out in an special circumstance, as with the approaches of the human inventive activity). In contrast as it is described in this present invention with the introduction of an exogenous, extrageneric zymogen (tissue or organism external and of other vegetable or microbial genus, enzymatic activity) and therefore being used here with this exposed finalities, as inventive activity, of obtaining the cyanogenic and related similar glycosides, plus of their "aglyconic" hydrolytic derivatives, the genin and also of the sapogenins. The transformation described in the present invention has the derived aglycones (the genin and the sapogenins), not toxic and the uses of these extracts or related compounds of the "sapotes" mentioned in the following cosmetic uses and in pharmaceutical dermatological compositions as the objective, without reported or industrial previous or current practice use to this present invention, being not used or of waste or of inadvertent potential, as natural profitable resources not taken advantage, in which not only the benzaldehydic genin extract are obtained but also to the sapogenins extract that contains the carbonylic hydroxylcompounds and apart from being used all of these in form of extracts or in purified form, with the same finality, which is the making of cosmetics and pharmaceutical dermatological compositions or in alternating substitutes or potentials uses, as in nutritious (as for example in flavouring or conservative agents), with different properties to the materials and products already existent, as described previously and later on.

The absence of the biochemical event, of the catalytic metabolic inability, typical of the kernels of the related "sapotes", is the benefit without being take in advantage as a human demand for a modern cosmetic, medicinal and nutritious resources obtained, separated, transformed, and manufactured, by means of the hydrolytic aglyconic, exogenous, extrageneric reactions, in to a volatile soluble and insoluble (to water) matter, with pharmacological properties, as are the volatile essences and those α-hydroxylcompounds, obtained by means of the inventive activity developed here in, and which are separated in forms of an oily and an another one soluble, (in water medium) as two fractions; the first one with characteristic aroma to the vegetable, the second with dermal properties, both mainly among other and the fact of the technological innovation here presented of their skilled uses, interceding in the obtaining of the cyanogenic and related glycosides of the "sapotes" being transformed by the enzymatic exogenous supplanting, of extrageneric added β-glucosidases by an external, peculiar, appropriate, convenient, appropriate and by ex-profess means, of different vegetable or microbial genus and in this way making possible their transformation and use of the both groups of extracts achieved, the genin and sapogenins; these turns out to be the reason of the present invention and as technical advantage over other known processes as the amygdalin one of the bitter almond which only transforms to the benzaldehydic genin with their endogenous, own enzymatic systems, without achieving the hydroxylcompounds with carbonylic characteristics as the carboxylic acid or as its related amide, presently the lucuminic acid and the lucuminamide (corresponding to the related derivables glycosides to the last aglycones).

The extra-generic enzymatic supplanting, a reason of the present invention, results as a different yielding process to those existent with a minimum cost in the financing of the process which is limited to the kernels of the related "sapotes" and the restitution and supplanting means of a appropriate, convenient, peculiar appropriate, extrageneric zymatic (enzymatic activity) suspension of β-glucosidases "emulsins", able to make the mentioned transformations (glucosidases systems) in all of the cyanogenic and related glycosides, transformation described later on. This profitable method arises as an innovative procedure by means of the treatment of the homogenized kernels of the "sapotes" that are the vegetable material that are not used in a more favourably way than as here mentioned and of the exogenous zymogen, of the reaction container (or reactor) plus joined of the set up and implements of products separations.

Other favourable uses different to the employments of this invention can be as breeding foot or implant, or the one used in another more revenue-yielding form of what it can be of the facts of these descriptions and of the precedent lipid recovery, related application of patent by the same author, as in the employment in inconsistent incomplete usuries and as rustic and traditional employments in relation to the uses that are possible to give in context to the present work, or what is worse, employments that are not able to separate the pharmacologically active matter of the constituents of the kernel that make them inappropriate, toxic (if they are ingested in food recipes) or unapparent to be exploited, and the power to be used in the processes described in this section and later on, and in the related application (ref. 68). The uses more profitable here described are the use of the raw materials and elaborated obtained by this work to make work up products of commercial use of employment by the society which uses ingredients of the kernels of the "sapotes", as here related, as to the derives aglycones or genin and sapogenins extracts, prepared cyanogenic and related glycosidic and plus the fixed lipidic extracts in total or partial composition and being exploited industrially as a renewable resources as that of the kernels, by means of their transformation to consumption products as cosmetics and pharmaceutical dermatological compositions or in alternating substitutes or potentials uses, (as pharmaceutical raw materials or in nutritious uses) and other uses already and later described. For this reason and that mentioned before (ref. 68), the use of the kernel of the "sapotes" as described previously in the present invention is a technical advantage with regarding to processes already known in which there are not used the resources and work up of the kernels of the "sapotes" in their entirety, being matter of waste of the fruit and very little for other purposes or their null or almost null use in profitable processes, as the transformation, obtaining and use in derives or extracts as that of the genin, (the benzaldehydic derived), free of chemical reactants, accompanied by a series of volatile substances that characterize the extractive volatile oils or essential oil and with the co-production of the sapogenins or the extract sapogenins composed by a benzylic alpha-hydroxylated acid and by the amide of this same last acid, that also are carried out by means of the resembling same process, reason of the present invention or in contrast with the use of mandelic acid obtained by means of chemical synthesis, with energetic reactions giving reaction mixtures, without obtaining the amide of these related acid, as in the other hand by the present invention. Another difference is in the resembling similar transformation of obtaining and the use of the sapogenins of the "sapotes" also achieved in a subtle way, by enzymatic biochemical reactions and by faint technique of separation, against the other processes to obtain "similar" inequivalentes products.

Another technical advantage of this invention is that there are also obtained the volatile oils of the "sapotes" (essential oil) as pharmaceutical ingredients and of nutritious potentials that don't exist in the "extracted form" just as "sapote" essence and less employee commercially, as the same that is characterized by its transformation and its obtaining processes, in its peculiar aroma to "sapotes", different from the isolated well-known, existent, natural benzaldehydic other vegetable aromas.

It is objective of the present invention is also to solve the problem of the rustic disposition that has been used in traditional cosmetics (or of beauty), medicinal and nutritious avails that distinguish the beneficial effects in the skin, the hair and in different affections and in diverse uses as in foods or in customs with the help of prepares of *Calocarpum, Chrysophyllum* or of *Lucuma* but without being identified its legitimates individual, isolated action of these principles separated in productive form as pharmacological, cosmetics, medicinal and nutritious principles, of the vegetable matter detoxificated in its employment. The cyanogenic and related structurally similar glycosides principles and derives, of genin, of sapogenins and as alternating agents from these mentioned effects (or synergistic) that of the fixed lipids extracts in total composition or in fractional or partial form, all coming from *Calocarpum, Chrysophyllum* or *Lucuma* and to incorporate them in effective cosmetic and current preparations or pharmaceutical dermatological preparations as solution to the technical problem in the use of similar very dislike products or in the traditional (rustic) use as technical novelties in cosmetic and pharmaceutical dermatological modern compositions that are efficient for the defoliation (desquamation) of the corneum (keratinized) superficial layer in a delicate way and of the epidermal renovation, including these effects to the keratinocytes at level of the hair follicle, which is stimulated in their growth and development, as well as in the prevention of the premature deterioration of the skin and of the hairy scalp and as agents that favour the percutaneous penetration together with a lipidic phase, being able to be formed by a hydrated lipidic lamellar phase or in vesicles of the liposomal type; or in uses equally compared as bacteriostatic and fungistatic agents, "in vitro" and "in vivo" which are reason of the present invention, facilitating alternating uses, as substitutes or potentials uses, as in nutritious uses, as pharmaceutical raw materials uses, as for example as prophylactic conservative matter, as flavoring, as aromatizing in foods and medicines, as organic acidifying agent, as anti-oxidizing agent, as buffering agent (of pH), as emulsifying agent, perfuming agent, vehicles or additives, etc., in connection with the related precedent patent application.

The "sugar" residues of the lucumin and of the related similar glycosides are also taken in advantage as spare alternating resources; in glucose and xilosa or as the disaccharide primaverose in the left over "zymogen" must residue of the amyloidal kernel hydrolytic extracted as a resource transformable metabolites in biomass, in the integral use of this vegetable mean.

DETAILED DESCRIPTION OF THE INVENTION

The present invention relates mainly with the cyanogenic glycoside, the lucumin and its related structurally similar glycosides, the lucuminamide and the lucuminic acid or for the corresponding hydrolysis aglyconic derives of these first ones, that are the sapogeninss and genin of *Calocarpum*, of *Chrysophyllum* or of *Lucuma*.

Present in the leaves, in the flowers, in the bark, in the sap and in the seed of the fruits their is a cyanogenic toxic glycosidic compound, the lucumin and also by the related structurally similar glycosides to the first one, the lucuminamide and the lucuminic acid. These are secondary plant metabolites of this family (Sapotaceae) and of the related genus *Calocarpum, Chrysophyllum* and *Lucuma*.

In a particular variant of the invention the cyanogenic and related structurally similar glycosides plus genin and sapogenins respectively as aglyconic derives of the first (but each one of these groups of extracts with independent, singular processes and obtaining); the first obtained by extraction and the aglycones derives obtained by chemical or enzymatic hydrolysis and then by extraction, being able to be of the bark, leaves, buds, flowers, of the sap, of the fruits shells and or of the fruit seed's kernel of *Calocarpum*, of *Chrysophyllum* and of *Lucuma*. Preferably in particular the vegetable tissue is selected of the kernels, as easily renewable resource, which are dried and degreased by techniques of lipidic expression and or continued by extraction of the remnant same lipids soaked kernel, with apolar solvent mainly, which are practiced with the purpose to recover mainly and to preferably be evade these fixed lipids for the task of obtaining the cyanogenic and related glycosides, if these are the extracts and made up of the subscribed to which is wanted to end up obtaining. To obtain those related aglyconic derives (of glycosidic hydrolysis) the fixed lipids don't interfere in the obtaining process, but is a profitable, revenue-yielding the preliminary recovery in anhydrous form of the fixed lipids before proceeding to the hydrolytic operation to obtain the aglycones, that involves the use of water.

The vegetable matter, as the kernels of *Calocarpum*, *Chrysophyllum* and *Lucuma*, in degreased and powdered form, when breathing these by the nose they irritate the respiratory tract and they make sneeze, signal of the sapogenic (foam forming) glycosides activities as reported. These last ones and the related aglycones can be prepared of the kernels, orderly in several ways in obtaining them, being the main ones those described previously and in the related application of patent, over the obtaining of the solid residual of the lipidic expression, this is in form of "expression crackling" solid residue of the squeezed liquid lipids and or as "degreased flour", solid residual of the solvent lipidic extraction, as vegetable residue in the obtaining of oils or fixed lipids of the "sapotes" by these mean.

The productive function of recovery of the fixed total lipids is carried out, which is the preliminary occupation, merely as an execution that profits dividends and that suits to be carried out before the operations of obtaining of the genin and sapogenins, this in a watery process, and the first process also of preferential evasion to the obtaining of the cyanogenic and related structurally similar glycosides if these last ones are the wanted end up products in the obtaining.

The sapogenic glycosides (that produce foam in watery, as the cyanogenic and related glycosides of the "sapotes") and their derived aglycone, are also attainable of the kernels like rough matters, flatly crushed or milled.

For the obtaining of the cyanogenic and related similar glycosides it is possible to use the vegetable matter directly as rough kernels, flatly milled or crushed or preferably being possible to use the total or partially degreased vegetable matter, as the solid residual that stays as remnant after the lipidic expression (partially degreased, with a small lipidic remainder) of the kernels and or more convenient as solid residual of the lipidic extraction of oils (to see the obtaining of the fixed total lipids of the expression or lipidic extraction of oils and of their residuals derives see the related precedent patent application of *Calocarpum*, *Chrysophyllum* or *Lucuma*. With the operation of degreasing in particular of the kernels with the process of lipidic expression a lipidic portion consistent in the obtained fixed lipids in total constitution (constituted by the fixed oils, the phospholipids and residuals lipidic glycosidic triterpenic and steroidal or here mainly calls the sterols (non cyanogenic) labile to these obtaining by the lipidic expression separation, removable by the techniques in use in the present invention and in the related precedent application for the degreasing of these vegetable matter (by expression and or extraction) as a fraction of oleaginous attainable substances in the preliminary procedures to another fraction of lipids derivables of the cyanogenic glycoside that correspond to the volatile oils described as the extract of genin; these last ones with alternating, collateral, secondary activity or in synergy to the main effects of this description and that are reason of this application and of the related application of patent by the same author.

As said in the previous paragraph it is possible to use the flatly, the whole, milled, crushed or rough kernels for the preparation of the aglycones derives of the cyanogenic and related glycosides, without some of these procedures of rough, milled or crushed, degreasing, extractive or hydrolytic treatments being dependent or restrictive one of the other in the raw material beginning used; being able to be initiate the obtaining of the derives aglycones of the rough (flatly milled or crushed) kernels or of the degreased kernels or of another preparation of the kernels or that of the glycosidic extract related to the cyanoglycoside or of this extract being used in some other ulterior stage in its purification.

The same as that noted in the previous paragraph it is possible to arrive to the related glycosidic extract to the cyanoglycoside or to this extract in some ulterior stage in their purification leaving of from the rough (flatly milled or crushed) kernels or the degreased kernels or of another different preparation from the kernels.

The vegetable matter of the kernels of the "sapotes" is constituted by lipidic material different to the fixed lipids. This lipidic fraction different from the fixed lipids consist of a volatile oil that are derived from the cyanoglycoside that are intimately bound to the structural matter by means of "sugars" that are united in carbohydrates chain in the sustenance of the germinal tissue (in the cotyledon) joined to the glycoside in the kernel. Some of these glycosidic substances consist of a disaccharide in union to hydroxylcompound with nitrilic character, or of carboxylic acid or as amidic derived of these last substances of the related glycosides that are hydrolysable of the carbohydrate portion to give the aglycones in special treatments, being able later on to be extracted, separated and isolated. In the present invention this hydrolysis to obtain the aglyconic extract is carried out directly of the kernels, independently of also having the possibility to be extracted the relates similar of the volatile oil from the isolated glycosidic matter coming from the same kernel's resources but obtained in another process, and then to this glycosidic extract to be practiced the hydrolysis to the related previously aglycones, in this including the volatile oil; these volatile lipids are recognized here as the genin extract and of another water-soluble one, the previous mentioned sapogenins extract of the "sapotes".

The "aglyconic" hydrolysis process of the present work is carried out mainly with the introduction of an enzymatic exogenous (external to the kernel's tissues [or of other tissues of the same plant organism]), extrageneric (of other vegetable or microbial genus) systems; however this hydrolysis, in the isolated kernel, is not carried out in natural common form, with its own enzymatic mechanisms of the same kernel of the "sapotes", prepared as a unique material independently, flatly milled (in a watery medium). Because this hydrolysis requires the introduction of a second enzymatic alternating exogenous, extrageneric, appropriate functional system, peculiar to achieve the conversion to those derives of the genin and sapogenins from the related glycosides of the "sapotes", and after this obtaining there are used separation technique of the hydrolyzate extracts. This aglycones derives conserve the alpha-hydroxylated characteristic, one of nitril (alcohol), a second of an amide (alcohol) and third oner of an acid (alcohol) respectively of the related glycosides of those that they come from. The first of these derives substances, of the previous mention, becomes a genin benzaldehydic, oleaginous and volatile, an odoriferous oil different to the fixed lipids mentioned previously, insoluble to the water, attainable by the enzymatic same last reaction or later on spontaneously from the intermediate cyanohydrin, (mandelonitrile) as hydrolyzate of the nitril glycoside (cyanoglycoside); being able the two other substances of the hydrolyzate extract, the amidic and acidic derives of the previous mention water hydrolyzate extract, as the same, separable and recoverable, dissolved in the watery means of the hydrolysis. In this way, there are obtained the genin and the sapogenins extract as a volatile extract respectively, the first ones with characteristic of essential oil the second with other pharmacological characteristics both of high importance to the present work, as having said previously and more ahead.

The genin is obtained as an aglycone of the lucumin, the cyanogenic glycoside and the sapogenins as the two other aglycones of the related glycosides, the lucuminic acid and the lucuminamide of *Calocarpum* or of *Chrysophyllum* or of *Lucuma* (or the referred "sapotes").

In another creation the cyanogenic and related structurally similar glycosides, those hydrolysis derives of the first, the aglycones, genin and sapogenins are derived preferably of the sapogenic (producing of foam) glycosides as the lucumin, the lucuminic acid, the lucuminamide; as benzaldehydic genin, and as an acidic and as an amidic sapogenins, of similar structures respectively of the related previous glycosidic predecessor, as obtained. These obtaining of the aglycones are possible readily achieved without being necessary to extract beforehand the related glycosides. To obtain the aglycones in isolated form and to separate them, being able to be started of the rough, milled kernels or of some other products of them, as degreased partially or totally solids residuals of the kernels as mentioned previously, without being restrictive any treatment in the obtaining of those raw materials derived in the previous mention, being able to use the kernels or the cotyledon flatly milled or crushed or if wanted the isolated related glycosidic extract or some ulterior stage in their purification may be used.

The sapogenins is constituted by volatile matter, the same as for the genin; these last ones, the volatile oils are used in the present invention like rubefacient agent and as a selective counter-irritatant of delicate epithelia (as that of the face and hairy scalp of the head), that opens the pores of the skin, used in cosmetics preparations or pharmaceutical dermatological preparations.

On the other hand the activities that are displayed by the sapogenins which are used as defoliative agent that promote the renovation of the skin and the stimulation of the development of the epidermis, including hair growth and in the retardation in its fallen, to combat the effects of the epidermal aging and the premature deterioration of the skin in topical preparations, also with action of harnessing of the percutaneous penetration. The property of harnessing of the oily phase percutaneous penetration of the sapogenins, in preparations in base of these are exhibited in watery solution ensambled with a dispersed lipidic phase or with a hydrated lipidic lamellar phase or of vesicles of the liposomal type that contain them and of the positive effects for the use in reiterated treatments, in the improvement of the skin and the deteriorated hair, and also with the variation of bacteriostatic and fungistatic effects that are also exhibited "in vitro" and in the skin by these substances.

The referred glycosides in the previous paragraphs are characterized to be β-D-diglycosides, lucumin consist of the absolute structural formula of ([6-O-(β-D-Xylopyranosyl)-β-D-glucopyranosyloxy]-2-phenylacetonitrile) and of the other two similar derived related glycosides, the lucuminic acid ([6-O-(β-D-Xylopyranosyl)-13-D-glucopyranosyloxy]-2-phenyl carboxylic acid) and the lucuminamide (6-O-(β-D-Xylopyranosyl)-β-D-glucopyranosyloxy]-2-phenylacetamide) or the derives of the cyanogenic as related similar glycosides of *Calocarpum, Chrysophyllum* or to *Lucuma*, which are mainly constituted by aglycones of the type of the alpha-hydroxynitrile, and of the derives alpha-hydroxylated acid and amide of this last acid, and by the carbohydrate (disaccharide), the primaverose as the "sugar" hydrolysis residue of the lucuminic related similar glycosides, in which different methods are used in their determinations, included the indirect method photometric and the direct chromatographic, being able to be qualitative, semicuantitativos or quantitative.

The cyanoglycoside, the lucumin of the "sapotes" and those included as the related structurally similar glycosides to the first, recognized as the lucuminic acid and the lucuminamide found in this present work with activity in front of ((3-glucosidases [amigdalases] and to other desnitrilases, hydroxynitrile liases or mandelonitrile liases) in union to other constituent of the exogenous catabolic complex enzymes systems that are absent or inactive in the stage of kernels, not germinal in the related "sapotes" core discovery of the present work. It has been found in this work that the lucumin in front of this exogenous catabolic glucosidases activity gives mandelonitrile and later on benzaldehyde; the lucuminic acid and the lucuminamide gives an acid and an amide respectively, similar to the mandelic acid and the mandelamide respectively; both the acid and the amide here found contain characteristic of hydroxylcompounds in alpha position to the adjacent carbonyl functional groups, as mentioned of the respective compound, alike to the glycosides where they proceed, structurally similar but cleavage from de "sugar" moiety.

The related glycosides, of not having practiced the "aglyconic" hydrolysis, can be obtained and separated too in an extractive different process for obtaining glycosides, independently of the former present hydrolytic enzymatic aglyconic derivation process.

The enzymatic hydrolytic aglyconic process can begin, without being dependent or restrictive, with the related glycosidic extract or in some other stage more advanced of its purification, these arrivals in the obtaining of the aglyconic hydrolytic derives being more elaborated and more expensive the obtaining if starting of these stages of elaboration from these related glycosidic resources, being able to start from some other primary kernel's bearing cyanogenic and related glycosidic principles. Much more convenient for arriving to the enzymatically hydrolytic aglycones derives is beginning from the derivation of some product of the rough kernels, flatly milled and or as solids residuals products, partial or totally degreased, as of the solids residuals products of expression and or of extraction, both lipidic respectively.

It is started from vegetable matter that does not have value or least commercial value as the leaves, the fruit shells or preferentially of the seed removed fruit, withdrawn of the pericarp and endocarp. Preferably, these last ones are used, to leave the lonely kernel, which are used. The vegetable matter is selected of which have changes in the coloration due to oxidation or to the degradation with saprophytic flora caused by excess of humidity. Of this selection they are dried off of the natural humidity of the fresh seed (without excessive drying), they are cut, mill or they are crush, they are degreased as indicated previously and it is extracted by means of solvents chemically pure, selected of water, alcohols preferably containing from 1 to 4 atoms of carbon and of esters containing from 3 to 6 atoms of carbon or by means of mixtures of solvents based up on any combination of the solvents mentioned, if its wanted to arrive the related glycosides to the cyanoglycoside.

When the cyanogenic and related structurally similar glycosidic extraction had concluded the extract is filtered and concentrated by evaporation to dryness at reduced pressure to give a primary extract of concentrated glycosides in accordance with the present invention.

In a particular variant the uses according to the invention are related to mixtures of similar glycosides to the lucumin which are obtained according to the present invention as a concentrated extract or as a dry extract for the later on indicated procedures in the examples 1, 2 and 3. The primary extract of previously mentioned glycosides is treated by the introduction of a apolar solvent or of intermediate polarity and after being shaken in it or the solvents that are miscible of preference with the primary solvent of extraction, as ethers or ketones of low molecular weight, in particular ethyl ether or isopropyl ether, acetone, ethylmethylketone from among the main ones. The quantity in weight of the apolar solvent or of intermediate polarity used is from 1 part to 100 parts of the solvent by the glycosides material of the primary extract here mentioned. The insoluble material and or the precipitate formed contain a mixture of the mentioned related glycosides structurally similar in semi-purificated form according to the invention.

It is possible to purify even more some of the related glycosides to the cyanoglycoside by recristalización or fractional crystallization of some by an accessible method with polar solvent or of water, or it can be used as a total extract, according to the procedures in the invention.

Even more, it is possible to purify the mixture of previous glycosides by means of the redisolution of the insoluble material or the precipitate in volumes that go from 1 to 20 parts of their weight in water. The water dissolution is extracted from 2 to 5 times with an alcohol that is scarcely soluble in water as the n-butanol or iso-butanol, which has been saturated with water, in proportions that can be for example of 1:1 in volume for each extraction operation. The alcoholic extracts are separated from the watery phases; they are combined and evaporated by reduced pressure. The residual of the evaporation is redisolved in 10 parts of their weight in water and dialyzed against pure water. The dialysate of the extract of similar glycosides to the cyanoglycoside is lyophilized and if necessary purify even more, the lyophilized is dissolved in the minimum volume of methanol, which is evaporated, and it is restored with absolute ethyl ether and the precipitate formed is gathered. The solid mixture is redisolved in the minimum quantity of water and they are practiced chromatography techniques of separation to be isolated as pure compounds, techniques as the proposed in the example 3.

The genin and sapogenins can be extracted of the transformed vegetable matter of the kernels treated directly or of the extracted glycosidic material enzymatically transformed, of the same treatment described before and more ahead and in the previous paragraph and, practiced to the concentrated extract of related glycosides or concentrated rich in related glycosides, independently of the more affordable treatments starting from the preparations of the kernels, rough, cut, flatly milled, or crushed and or degreased partial or totally; mainly this procedure is practiced of what is left of solid vegetable residual product of the of the lipidic expression or more preferably of what is left of solid residual of vegetable matter of the lipidic extraction of the kernels.

The genin and sapogenins in accordance with the present invention are obtained as aglycones hydrolyzates with the methods proposed here, starting from the prepared kernel or of the semi-purificated extracts of related similar glycosides to the lucumin; this last obtaining procedure by starting of the later procedural extraction, of the cyanogenic and related glycosides extract is independent of the hydrolytic aglyconic procedure that is by means of the direct treatment of prepared vegetable matter of the kernels (cut, milled, or crushed) or by means of the treatment to the solid residual of lipidic expression of the same ones that are mentioned previously and or of the solid residual product of the lipidic extract, the flour without fat (or degreased partial or completely kernels, respectively); being this last resource the most advantageous for the productive recovery of the entirely of the lipids precedent to these treatments, in the integral use of the seed.

To cleavage the genin and sapogenins of the semi-purificated cyanogenic and related glycosidic extract it is proceeds preferably of some of the following preparations of the kernels; as of vegetable matter without processing, as a whole, flatly milled or crushed, or it can be used the solid remainder of the vegetable matter after the lipidic expression (or in other words of the "expression crackling") or of the solid remainder of the lipidic extraction (or the degreased flour); this is made by means of the breakage of the glycosidic linkage of union to the disaccharide, by acid hydrolysis as it is made conventionally, which takes place with such as the use of sulphuric acids or concentrated or diluted halogenated acids. The main halogenated acids used in the present work are hydrochloric, perchloric, tricloroacético acids, which are used in similar form to those described in the previous references.

In another means of enzymatic hydrolyzing forms, proteic extracts are used or purified preparations or without purifying, isolated or without isolating of the same catabolic zymogens without this being a restriction on the hydrolyzing form, or in the origin, or in the enzymatic used form, being able to be of microbial origin or vegetable coming from tissues of diverse species including several types of kernels or of different kind tissues, of oneself exogenous vegetable or of several vegetables or microbial; all peculiar, appropriate, convenient and appropriate as of leaves, shafts, bark, pulps of the fruits among other and of the seeds and kernels in this way mentioned. However it is needed of a specific or a not specific adequate, convenient, appropriate and peculiar enzymatic systems which are required as having said previously, different to the existent endogenously inactive, or not functional, or not existent of the related "sapotes" that can take over the transformation, for the purpose of this work, which are in exogenous vegetables tissues or microbial cells; which catalyze the transformations to free "sugar" and the particular aglycones of the "sapotes", being this series of reactions the most profitable forms for the objectives of the present invention followed by separation and, isolations and if its wanted ulterior purifications.

In a hydrolysis type that uses vegetable enzymes and that is carried out in watery buffered solution, preferably with acid medium, in the vegetable matter of *Calocarpum, Chrysophyllum* or *Lucuma*, that it contains these types of zymogenic ferments or proteic extracts of enzymatic systems or purified enzymes matters or purified preparations or without purifying, isolated or without isolating, which are peculiar, adequate, convenient and appropriate of beta-glucosidasas exogenous as the same as the glucosidasas of other vegetable genus which catalyze the hydrolysis of its own glycosides (of the same genus) but that it is also possible to use them exogenously in another generic type of vegetable active glycosidic substrates that lacks the own required (endogenous functional glucosidasas) or enzymatic potential as in the glycosidic, cyanogenic and related glycosides, substrates of the genus of the referred "sapotes." These exogenous systems of "emulsins" hydrolyze beta-glycosidic linkage in monomeric or dimeric units of "sugar" and in hydroxylcompounds, or the aglycones, which are hydroxylcompounds that are benzylic (phenylic) with nitrilic or later on aldehydic characteristics in the case of the hydrolysed lucumin glycoside; on the lucuminic acid or lucuminamide glycosides hydrolysed with these same acid and amidic character but aglyconic respectively; all of this of applications and functionalities in diverse specialties.

These transformations depend on the systems kinetic properties of the zymatic operation, of the enzymes activity, of the reaction speed, of the optimal pH, of the temperature to "culminate" in the chemical mentioned products.

As in the amygdalin or the prunasin coming from the Rosaceae family of the genus *Prunus* like *P. amygdalus* and *P. serotina*, as the benzaldehyde is obtained by other techniques, using enzymatic endogenous, "own" mechanisms, characteristic of this kernels of this vegetable groups in exhibition, arriving to this substance as aglycones of mandelonitrilic characteristics and later on becoming benzaldehyde; situation that equally happens in the lucumin from the "sapotes" for exception that is necessary the introduction of exogenous (external) enzymes, extrageneric, of another genus for the obtaining of significantly useful results, and for their applications in cosmetic, pharmaceutical and as the same in foods and in other substitutes uses, condition that is not gotten with the own endogenous glucosidases ("emulsins") of the genus of the related "sapotes" (see example 8).

For hydrolysis of the acid and amidic glycosides related to the lucumin of the "sapotes" or more specifically to the lucuminic acid and the lucuminamide respectively using vegetable exogenous enzymes, extrageneric (of peculiar, adequate, convenient, appropriate origin), the aglyconic derives are obtained, as alpha-hydroxylated, acid and the respective amide of the precedent glycoside, promoted by exogenous hydrolases, extra-generic, well right managed of other genus that cleavage the disaccharide as freed glycone, from the related glycosides, liberating the sapogenins as the referred aglyconic products, one an acid and another an amide correspondingly. These aglicionas being separate as a sapogenins extract mixture (scrambled with the genin). The benzaldehydic genin are liberated of the lucumin (coming of the remaining related glycosides), and firstly separated of the sapogenins; both groups of substances, genin plus sapogenins are obtained as a volatile extract in union that is possible to separate in its components by its different physical properties.

The suspension obtained by "aglyconic" enzymatic hydrolysis from the cyanogenic and related similar glycosidic substrates of the "sapotes", using exogenous, extrageneric zymogen and using special in accordance and separation techniques, to set apart these substances, which gives as a result a suspension/solution that also forms very apparent foam, formed by the soluble sapogenins, scrambled by an insoluble material to the water, oily and with characteristic aroma to the same plant conformed by the genin, like they are obtained in particular in a variant of the invention that is the one of obtaining aglycone hydrolytic products of the cyanogenic and related similar glycosides of *Calocarpum, Chrysophyllum* and *Lucuma* by the preparations of (β-glucosidasas, external, exogenous, extragenéricas, adequate ["emulsinas"] of another genus, microbial or vegetable), being added ex profess, in buffered conditions of acidity, pH, concentration and temperature controlled. This is with the introduction of a second enzymatic of vegetable (or microbial) different species systems, unspecific or specific enzymatic over the existent glycosidic substrates of the related "sapotes", as the alternating systems that are demonstrated in the examples 4, 5, 6, 7 and 8.

The genin and sapogenins of *Calocarpum* in this way obtained have haemolytic activity to high dilutions mainly those that are soluble to the water.

For hydrolysis of the glycosidic linkages as made by the exogenous (β-glucosidasas ("emulsins"), here mentioned and some other ones not described here, to these cyanogenic and related similar glycosides but taken place at acidic buffered conditions that make possibly the transformation to the specific aglycone products, the benzylic hydroxylcompounds, carbonylic and one with aldehyde (benzaldehyde) character; one of the first with acid and another of amide characteristics, both related corresponding with characteristic similar to mandelic acid and the mentioned mandelamide respectively, and another derived of the mandelonitrile recovered as benzaldehyde corresponding to those of the predecessor glycoside moiety. These aglycones, the genin and the sapogenins of which the most abundant are volatile substances that resemble to be substances as the benzaldehyde, the mandelic acid and mandelamide respectively of *Calocarpum, Chrysophyllum* or *Lucuma* by the unspecific or specific exogenous enzymatic action and or by alternating chemical hydrolysis process, and by separation techniques for the isolation of this type of acquired compound.

In a particular variant of the invention is by the one that uses enzymatic exogenous systems of non own (not endogenous) β-glucosidasas of *Calocarpum, Chrysophyllum* or *Lucuma*, coming from another vegetable species mainly acidic and not acid "emulsins" in buffered acid medium, like it is demonstrated in the examples 4, 5, 6 and 7 with which the insoluble and soluble, to the water aglycones are obtained respectively, the genin and the sapogenins, mentioned previously.

The acid buffered means is achieved using tampons of acid citrate, acetate or acid phosphate and mixtures of these among others or the one proportionate by different purified or not purified preparations of vegetables tissues, isolated or without isolating that mainly contain this pH and glucosidases of which it is preferred the acid glucosidases (coming from vegetables).

Finally the reaction that takes place on the cyanogenic glycoside (alpha-hydroxynitrilated) is the deglycosilation in the cleavage of the "sugar" moiety, regulated by beta-glycosidases that include enzymes that catalyze the same reaction and subsequent chained reactions in the integral reaction from beginning to the end, as they can be hydrolases, as those alpha-hydroxylases, the prunasin hydrolases, continued by the mandelonitril liases; which all take place in a similar way to obtain this product, the mandelonitril that later on becomes in benzaldehyde (desnitrilated) and to the other two related aglycones, the acid and the other amidic of the "sapotes", (deglycosilated); carried out by enzymes that account mainly to glycosidases of another exogenous, peculiar, adequate, convenient species; as the acid hydrolases, hydroxylases and hydroxynitriliases, belonging to these systems here used and described, able to carry out the reactions described on of the species related of the "sapotes" with this afunctional activity, diminished or inactive as having described in the examples 4, 5, 6, 7 and 8.

After having taken place the enzymatic reaction to ambient temperature or between 15-60° C. and with agitation for some minutes, later on it is used some appropriate technique of separation of the genin and sapogenins, which can be by filtration, extraction, or by some other technique that uses the capacity to separate to this emulsified mixture (or suspension) of components by means of gradients of quick heat/boiling, applied to the reaction mixture like mentioned previously.

The isolation of the hydrolytic enzymatic reaction mixture of products is carried out when they undergo quick heat in a recovery and isolation device; the separation is carried out among 80 to 110° C.; leaving the products of degradation of the primaverose that are to the glucose and the xilosa or the whole primaverose, depended in the type and force of the hydrolysis.

The genin and sapogenins in the previous achieved way are obtained between watery medium; the genin are acquired as an insoluble liquid mixture in this mean, which are separated by using this property. In the watery phase are the sapogenins which are soluble and they separate from watery means by extraction with apolar solvent or of intermediate polarity, immiscible to water, being able to be by several extractions, from 1 to 5 approximately, to complete the extraction of the watery solution isolated from the reaction and separation.

Solvent are used such as those previously mentioned for the execution of the previous paragraph, using a same volume, as for example, of absolute ether for the extraction of the sapogenins solution, this is later on when they have been separate and isolated from the previous water medium of hydrolysis and of the whole hydrolysis recovered extract with the exclusion of the genin respectively. The quantity of the apolar solvent or of intermediate polarity used can be of fractions or of 1 part to 5 parts or by greater quantity of the solvent for 1 part of the volume to be extracted. The organic phase in this way extracted contains the sapogenins mixture which is concentrated to dryness using vacuum, a dry extract of sapogenins as a concentrate is obtained according to this invention. The organic extract of sapogenins is concentrated by evaporation and is conform as a solid concentrate of sapogenins. It is possible to use some appropriate technique of crystallization in their isolations.

Of being required, the sapogenins can be purified by some appropriate technique of crystallization with alcohols from 1 to 4 atoms of carbon and mixtures with water.

This form of arriving to the genin and sapogenins is only as form of indication, without these implying to be a restriction in the raw material of origin used as it has been explained previously, being able to start in several ways of prepared kernels of the related species of the family Sapotaceae and as the same being able to carry out several types in the way of hydrolyzing like mentioned previously or as in diverse forms of isolating or in the varied extraction form and in those of separation of the isolated products and in the ways described here like an exemplification mean and of other capacities to obtain of these active substances mentioned in the present invention.

In a variant of convenience, the mentioned sapogenins is selected of those that do not contain ionized carboxylic acid groups and of their corresponding metallic salts, especially of calcium and of sodium, to complete the present invention.

In still another variant of the present invention the vegetable matter of *Calocarpum, Chrysophyllum* and *Lucuma* mentioned previously are selected of generic groups consisting of *Calocarpum sapota, C. mammosum, C. huastecanum, C. viride, C. odoratum, Lucuma domingensis, L. stahliana, L. dussiana, L. cuprea, L. campechiana, L. obovata, L. hypoglauca, Chrysophyllum mexicanum, Ch. cainito*, here related as the "sapotes."

In another creation more of the invention the cyanogenic and related glycosidic extract and of their previously mentioned aglyconic derives are obtained by methods that are described later on like indication forms but these do not imply some limitation in the reaches of the present invention and in the forms of obtaining of the active ingredients of *Calocarpum, Chrysophyllum* or *Lucuma* and their uses in cosmetic, dermatological pharmaceutical preparations and the possibility of being used in nutritious uses or as alternating substitutes.

In accordance with the facts exposed in the present invention which are related with the use of at least a derivative of *Calocarpum, Chrysophyllum* or of *Lucuma* from among the fixed lipids or fraction of them, of the volatile oils or fraction of them, and of the rest of volatile substances from among the genin and the sapogenins or fraction of some of them and of the similar corresponding to these and the related glycosides to the lucumin and structurally predecessors of the derives aglycones, of where the two last previous groups of substances come from or fraction of some of them in any form that could be presented: As vegetable residual products of the expression of the lipidic material; in form of solid residual of the extracts of the lipidic vegetable matter; or in another raw material form rough vegetable; in form of hydrolytic products using acids or bases; hydrolyzing using exogenous enzymes of natural vegetables of diverse tissues of the same or of several vegetables or of microbial origin or by the use of ferments or zymogenic proteic mixtures or of diverse preparations of the previous ones; conformed by vegetable matter coming from kernels or of different vegetables tissue with zymogenic character, or as the same of vegetable or microbial matter extracts, as an alive zymogen or in form of microbial active extract, or some preparation or of several of the same ones, incorporated in form of rough substances, semi-purificated or purified coming from the same vegetable matter of *Calocarpum, Chrysophyllum* or *Lucuma* and or of another vegetable or microbial species in which it can be found these compounds that catalyze the transformations of mentioned "aglyconic" hydrolysis, to be used in cosmetic preparations or pharmaceutical dermatological preparations, (or nutritious or other substitutes uses) resolved particularly as delicate defoliation agents of the corneum superficial (keratinized) layer and of the gradual renovation and stimulation of the development of the epidermis, to counteract the effects of the epidermal aging and of the prevention of the premature deterioration of the skin and of the hair and scalp including these effects to the keratinocytes at level of the hair follicle, as the stimulation of the growth of the hair; and their are also concomitant effects as harnessing percutaneous agents and as local bacteriostatic and fungistatic agent in the skin or in cosmetic or pharmaceutical dermatological preparations, or in uses as pharmaceutical preservatives or nutritious complements substitutes like said previously and like it is demonstrated in the examples 9, 10, 11 and 12; and of the example 5 of the related patent application by the same author; without these demonstrations imply some restrictive limitation of the present invention.

According to other facts the invention further more provides methods of manufacturing cosmetics or pharmaceutical dermatological products developed in particular as delicate defoliating agents that promote the gradual renovation of the skin and the stimulation of the development of the epidermis and to combat the effects of the epidermal aging and the premature deterioration of the skin including the growth of the hair, with a retardation in its fallen, in preparations of topical application with activity of harnessing of the percutanea penetration, and also of the bacteriostatic, fungistatic varied effects in the skin and in the preparations of topic use, methods that comprise the use of at least one cyanogenic or related structurally similar glycosides in question or of their corresponding genin or sapogenins or of their components in isolated form or as aglyconic derives of the previous glycosides, of the whole or fractionated portion of fixed total lipids or vegetable extracts of these last ones or of the corresponding expression products or products of chemical hydrolysis of the last glycosides in pure or impure form or fraction of some of them or as they can be transformed or as products, being able of these to be contained in a hydrated lipidic lamellar phase in which they are present, prepared with appropriate vehicles or transporting excipient, cosmetics or pharmaceutical dermatological or of other types and for other uses. In a variant, these methods comprise firstly that at least partially they are incorporate at least one of the mentioned related glycosides structurally similar to the cyanoglycoside, genin and or of at least one component of the sapogenins respectively of *Calocarpum*, *Chrysophyllum* or *Lucuma* or their corresponding vegetable extracts or hydroxylated products and or related carbonylic aglyconic hydrolyzate of the corresponding glycosides or as solid residual products of lipidic expression, or as solid residual product of the lipidic extraction or as aglyconic hydrolyzate of the rough, milled or crushed kernels matter, in which are present in some way in preparations of cosmetic or pharmaceutical dermatological in a hydrated lipidic lamellar phases or in vesicles of the liposomal type alone or with some active other ingredient of the "sapotes" or pharmaceutical before mentioned before or with established pharmaceutical ingredients, and then prepared with excipient appropriate vehicles or adapted transporters being able to be used the own lipids of *Calocarpum*, *Chrysophyllum* or *Lucuma* to form the hydrated lipidic lamellar phases. The fixed lipids and their residual solids products of this vegetable genus are reason of another related application of patent by the same author, as mentioned previously.

The compositions used in the methods of the present invention can also contain a variety of optional ingredients forming the appropriate excipient vehicles or appropriate transporters that are added to the active ingredients of *Calocarpum*, *Chrysophyllum* and *Lucuma* referred in detail in the present and in the related application of patent on of the fixed lipids of these genus of the family Sapotaceae.

The compositions that are used in the methods of the present invention can preferably also contain a cosmetic or pharmaceutical dermatological acceptable vehicle, solid, semi-solid or as liquid, that can acts as diluents, as dispersing or transporting of the active ingredient or active ingredients in the related exposed compositions or not exposed here.

The term appropriate excipient vehicle in cosmetic or pharmaceutical dermatological transporters or as constituent of some substitute as nutritious article, as used in the present means that the substance or active substances or the inert ingredients that the term describes are convenient and appropriate for the use in human without having toxicity, incompatibilities, instability, diffused irritation, allergic answers, or adverse similar or different answers in its way of administration.

The appropriate cosmetic or dermatological pharmaceutical vehicle can comprise of 0.1% to approximately 99.9999%, preferably of 25% to approximately 99.99%, more preferably of 50% to approximately 99.99% and a lot more preferably of approximately 75% to approximately 99.99% and still a lot but a lot more preferably of 85% to approximately 99.9% in weight of the composition.

Acceptable, appropriate vehicles include water for example, emollient and or lipophylic or hydrophilic moistening, surfactantes (emulsifying agents), thickening agents, powders, polymers, resins, plasticizing, filler agents, lubricant, ligands disintegrating, solvent, cosolventes, buffer pH systems, preservative or conservative agents, sweetening/colouring agent, tints and pigments all of dermatological pharmaceutical or in their case of cosmetic or nutritious grade.

The water can be employee in the compositions described in the present and in other preparations not here presented as vehicle. When the water is used as vehicle the composition can be in form of solutions or dispersion, in emulsion, or in suspension form or as creams; or as previously mentioned being parts of a lipidic lamellar phase that previously has been hydrated, being able to contain the active ingredients of *Calocarpum*, *Chrysophyllum* or *Lucuma* in hydrated lipidic lamellar phases composed in the lipidic phase with genin and or in the hydrated phases of sapogenins; the hydrated lipidic lamellar phase being able to be conformed by the related glycosides to the cyanoglycoside; the lipidic phase of the liposomes or of the hydrated lipidic lamellar phase being able to be formed by the fixed lipids in whole or fractional form or by the volatile lipids or fraction of these of *Calocarpum*, of *Chrysophyllum* or of *Lucuma*, these mentioned fixed lipids being reason of another related patent application by the same author.

The emollient and or the moistening lipophylic or hydrophilic phases can include esters, fatty acid, alcohols, polyols, hydrocarbons, silicones, waxes, triglycerides, polymeric mixtures (gels), from among the main ones.

Other objects, characteristic and benefits of the invention are clearly apparent of the following explanatory description with respect to several examples that are given only as an illustrative mean; consequently in any way limit the reaches of the vast scope of this invention.

In the examples that the units are not indicated, they are expressed in percentage in weight unless some other units are indicated. In the case of extracts, the percentages (or weigh) are expressed in dry weight of the extract.

In the examples 2, 3, 4, 5, 6, 7, 8 and 15 their are implied preparation that contain the products of the fixed, residual and current lipids of the "sapotes" that are included by their activity, glycosidic content and or in having genin and sapogenins derives, carried out as residual products of expression or extraction, both lipidic and as current whole lipidic component; as the same by fractions or portions of the total lipids of current use which are included by the synergistic effect that they give to the sapogenins and genin, all of *Calocarpum*, *Chrysophyllum* or *Lucuma*, in the renovation and development of the skin and in the stimulation of the growth of the hair, apart from the mentioned other activities that are also reasons of this and of the precedent other invention by the same author, for what it is required of consulting the application of related patent.

EXAMPLE 1

Preparation of Glycosides Concentrated Extract of *Calocarpum* (*Chrysophyllum* or *Lucuma*)

150 g of dry kernels of *Calocarpum sapota* (or *Chrysophyllum* or *Lucuma*, of the related species) that have been pulverized and degreased to an end with a apolar solvent, are macerated in 2 lt of ethanol, the mixture is refluxed for 2 hrs; the solution filtered and recovered. The residual is extracts twice again but with 1 lt of ethanol, they are filtered and joined the three filtrates and concentrated on a rotatory evaporator to a volume of about 100 ml. The recovered is constituted as a raw rich extract of glycosides.

The raw rich concentrated glycosides extract can become semi-purified in the following way. The extract of previous glycosides is mixed with 200 ml of ethylic absolute ether. The insoluble material to the ether is recovered by sedimentation, decantation or filtration and cooling. It is dissolved in 100 ml of water and the solution is extracted twice with 100 ml of n-butanol saturated in water. The butanolic phases are combined, concentrated and evaporated at vacuum. The residual mixed in 200 ml of ethyl ether and the residual recovered by filtration.

EXAMPLE 2

Preparation of a Glycosides Mixture, of Cotyledons of *Calocarpum* (*Chrysophyllum* or *Lucuma*)

1 kg of fresh powdered degreased cotyledons of *Calocarpum*, (*Chrysophyllum* or *Lucuma*) are taken and macerated in a mixture of 2 lt of methanol/water to 50% in a boiling water bath for ½ hour. The suspension is not recovered, the residual is subject to the previous extraction treatment for 1 times more, and the suspensions in this join way obtained are separated by filtration in hot. This extract is concentrated to the minimum volume approximately 2 lt. The purification procedure is as described for the example 1, being the subsequent extraction with 1 lt. of n-butanol and it is continued with that isolation procedure.

EXAMPLE 3

Purification of Glycosides of Cotyledons of *Calocarpum* (*Chrysophyllum* or *Lucuma*)

The procedure is as described for the example 2. Florisil® (50 g) is suspended in 100 ml of water and the mixture is placed in a glass column with a cock for elution.

The resin is regenerated with 100 ml of diluted hydrochloric acid 1:3 until the eluent maintains acid pH. Then the resin is rinsed with methanol and later to neutral pH with 500 ml of distilled water.

4.7 g of the glycosides mixture obtained in the example 2 is dissolved, in a constituted mixture of 30 ml. of water and 10 ml. of ethanol and then the solution is passed through the column with the resin. 300 ml are eluted, with water 50 ml in 6 fractions. The fraction 2 contains a main spot in thin layer chromatography, in a precoated plate (Merck-60F254), eluted in the same way as the column and developed with sulphuric acid-naphtoresorcinol. This fraction is rotatory evaporated and it is extracted with 20 ml n-butanol, separated and the organic phase concentrated by rotatory evaporation at vacuum. The concentrate is restored with 5 ml of methanol for later to be tried to crystallize. A crystalline powder, 0.710 g is obtained that responds to the glycosides tests and for carboxylic acid.

The fraction 3 obtained of the column is monitored in a similar way to the previous one, it is concentrated, it is extracted and practiced the concentration by the same techniques as that for the fraction 2. The concentrate is restored with methanol, and as the same crystallized by techniques practiced with which 0.581 g of a glycoside is obtained that responds to the tests for glycosides and amides.

The fraction 4 and 5 obtained of the column monitored by the same chromatography technique of thin layer, being found a compound with less polarity. This fraction recovered by the same concentration-extraction techniques as for the previous fractions but with the difference that the concentrate is restored with a mixture of 5 ml. of water-acetonitrilo (9:1) and it is practiced techniques of crystallization. A glicosido, 0.752 g is obtained, in form of crystalline plates, that responds to the glycosides and nitriles tests.

EXAMPLE 4

Preparation of Genin and Sapogenins of *Calocarpum* (*Chrysophyllum* or *Lucuma*), Using Semi-Purificated Exogenous Enzymes 750 g of new (immature) leaves of Hevea sp taken. which are crushed to a fine powder in dry, frozen in acetone to −30° C., later are placed in a buffered Tris-HCl solution from 50 mM to pH 7.0 after which they are homogenized in a. mechanical blade mixer for 10 min. and it is squeezed through a mesh of 6 layers of gauze cloth. The filtrate is centrifuged to 8,000×g for 90 min. the resultant supernatant liquid is fractioned using gradients of concentration of $(NH_4)_2SO_4$, the precipitate from 30 to 80% saturation is gathered by centrifugation to the previous same parameters; it is re-suspended in the minimum volume of the previous buffered solution and it is dialyze against the same solution.

The procedure of obtaining of the glycosides of the "sapotes" is accomplished as for the example 2, but the double of "sapotes" kernels is used; the procedure for its hydrolysis is made to ambient temperature with 250 ml of deionised water to which is added the previous mentioned buffered solution with the mixture of soluble proteins including the semi-purificated glucosidasas of Hevea.

The activity of the glucosidasas of Hevea toward the cyanogenic and related similar glycosides of the family Sapotaceae is determined at the beginning of the stage (basal), intermediately and after the period of incubation that is of approximately from 20 to 30 min. Once the degradation of the glycosides and the formation of glucose has ceased with the concomitant liberation of the aglycones has finished. These reactions are considered by means of the glucose determination on aliquot of the mixture of reaction, using the Merck GOD-POD "kit" (for further information see the insert) being able to use a curve of calibration of glucose or when changes does not take place in the optic density value in of the series of aliquot of reaction, time that is considered as end of the reaction, using the previously mentioned buffered solution with the mixture of proteins of Hevea as the blank. The previous mixture is subjected to quick separation by means of a sudden rise in the temperatures until it boils, in a prepared device with a recovery resource; the genin and sapogenins are recovered in the first fractions gathered. The first fraction recovered, 150 ml, containing most of the expected extracts. The separation and recovery of the genin is accomplished in a separator funnel at 5° C., as an oleaginous top fraction in the watery solution. The recovery of the sapogenins mixtures of the watery fraction is accomplished by extraction with 300 ml of ethyl ether in three times, the extracts are joined and concentrated to dryness. With the purpose of purifying the sapogenins, they can be crystallized using an appropriate technique.

EXAMPLE 5

Preparation of Genin and Sapogenins of *Calocarpum* (*Chrysophyllum* or *Lucuma*), Using Semi-Purificated Enzymes of *Prunus vulgaris*

*Prunus vulgaris* kernels of the same variety, 600 g are used. First the seed is sterilized with a sodium hypochlorite solution to 0.5%, (w/v) dried off with filtered air. The seeds are removed of the endocarp to get the kernels. They are stored, homogenized, extracted and semi-purificated at the same 4° C. conditions.

The previous kernels cut by the half with a scalpel in a Tris-HCl 0.1 M, to pH 6.0 with 4 g of PVP buffered solution plus 6 g of glass pellets are homogenized in a mortar. The homogenized filtered through 6 layers of gauze cloth and the filtrate is centrifuged by 90 min. to 8,000×g. The supernatant is eliminated of the glass pellets and of the lipidic phase. The intermediate supernatant is decanted and re-centrifuged to the same parameters and dialyzed against 2 lt of a 0.01 M Tris-HCl buffered solution to pH of 6.0.

The obtaining procedure and of hydrolysis of the glycosides of the "sapotes" is accomplished as for the example 2 and 4 respectively except that the hydrolysis is made to ambient temperature with deionised water to which is added the previous mentioned buffered solution with the mixture of soluble proteins including to the glucosidasas of *Prunus vulgaris* semi-purificated.

The activity of those (exogenous β-glucosidasas of the genus *Prunus* on the cyanogenic and related glycosides plus of the recovery of the genin and sapogenins of the family Sapotaceae of the referred genus is taken after as for the example 4. An amygdalin standard is used using the extracted proteic fraction as mean of monitoring the enzymatic reaction activity recognition throughout the beginning, intermission and termination and of the final isolation process.

The amygdalin hydrolase, the prunasin hydrolase, the mandelonitril liase plus of some other isoenzymatic groups or some multiple enzymatic forms that catalyze the degradation of the amygdalin to hydrogencyanide and benzaldehyde are extracted, semi-purificated and recovered as a chemical properties and similar molecular weight enzymatic complex system in a combined proteic suspension by means of centrifugation, at a certain pH of the homogenized, made and extracted at 4° C. of the peach kernels, which give as resulting product to three main derived compounds of the exogenous substrates present of the family Sapotaceae (*Calocarpum Chrysophyllum*, or *Lucuma* of the related species).

EXAMPLE 6

Preparation of Genin and Sapogenins of *Calocarpum* (*Chrysophyllum* or *Lucuma*), Using Vegetable Exogenous Extrageneric Zymogenic Ferments, in an Acidic-Buffered Medium The extraction procedure, recovery and isolation of the zymogen is as described for the example 4 with the variant of the use of a homogenized of 450 g of fresh leaves of Citrus *vulgaris* in a means of acid citrate to 5% as agent zymogenic. The procedure of obtaining of the cyanogenic related glycosidic substrates of the "sapotes" is as for the example 2. The hydrolysis procedure is as described for the example 4 and 5 except that the two extracts added, the zymogenic plus that of the substrate are homogenized to ambient temperature with a 5% acid citrate in deionise water and they are left among 35-50° C. with agitation for 15 to 30 minutes more. The recovery of the genin and sapogenins are as for the example 4.

EXAMPLE 7

Use of Vegetable Exogenous Extrageneric Zymogenic Extract, for the Preparation of Genin and Sapogenins, Taking Advantage as Substrate the Solid Residual of the Lipidic Extraction of *Calocarpum* (*Chrysophyllum* or *Lucuma*)

1 kg of degreased " " flour of kernels of *Lucuma mammosum* (or some other species related of the genus *Calocarpum*, *Chrysophyllum* or *Lucuma*) obtained as solid residual product of the (expression and or) lipidic kernel extraction (using not polar solvent as the mean), is taken advantage, as substrate in the exogenous zymogenic reaction.

As zymogenic ferment preparation of fresh seeds of *Citrus medica* are used as the same way as obtained for that of the example 5. A preparation of % kg of a homogenized is used, preferably fresh seeds.

The hydrolysis and obtaining procedure to the genin and the sapogenins are as those for the example 6, the substrate is putted in contact with the zymogenic prepared in 2.5 lt of deionise water, it is homogenized to ambient temperature (15-40° C.) by half hour, it is isolated and the products recover as for the example 4.

EXAMPLE 8

Demonstration of the Activity of "Emulsins" of Different Exogenous, Extrageneric Zymogenic Systems on the Glycosides Found in the Kernels of *Calocarpum* (*Chrysophyllum* or *Lucuma*) Treated in a Different Way In this example the fermentative zymogenic activity of different "emulsins" resources is demonstrated on four different pulverized states (stages) of the kernels: in fresh, dried, in form of "degreased flour" of lipidic extraction (by means of extraction with polar or of intermediate polarity solvent), and as "expression crackling" (by means of the lipidic expression gotten as the residual product not completely degreased, of *Calocarpum sapota*, (or species related of *Calocarpum*, or of the genus *Chrysophyllum* or *Lucuma*); and the employment of alternating, exogenous, external different enzymatic systems, extragenéricos, as that of the procedures used in the examples 5, 6 and 7 of this application, contrasted against the same procedures without using enzymatic exogenous (external zymogenic) systems.

The two forms of obtaining the kernels of the related "sapote" as the "expression crackling" of lipidic expression and as "degreased flour" of lipidic extraction is as they are obtained respectively in the example 1 and 2 of the related patent application, about the lipids expression and of the oils extraction of the "sapotes" and of the use of the residuals of these two processes in the obtaining of the cyanogenic and related glycosides and of their genin and sapogenins derives.

Twelve procedures are made to the four stages of the powdered kernels of the related mentioned "sapote", practicing them the procedures of the glycosidic hydrolysis using the zymogens as that of examples 5, 6 and 7 of this application, with the introduction of the exogenous last mentioned agents, in comparison against the same practiced procedures, to the same powdered four different stages of the "sapotes" kernels but without the introduction of any external zymogenic agents; the first one in fresh state (stage), the second in dried state (for no more than a year of storage), the third state as "expression crackling", and the fourth state as "degreased flour".

1 kg respectively of the powdered kernels of the related "sapote" are used as the each different stages or forms of trying the kernels, in these demonstration of the activity of exogenous "emulsins" of different enzymatic extrageneric systems against each one in test: as rough crushed in fresh state, rough crushed in dry state, in form of "degreased flour" and in form of "expression crackling" respectively; for each stage tested, practiced to the four groups of zymogenic activities. As the same, their are made equal procedures using 1 kg, for each test practiced in the different stages but without the introduction of an external zymogenic agents to the kernels of the related "sapote". Following, after a time from 15 to 20 minutes, all of the tests are separated as for the example 4.

The sapogenins are quantified by means of the yield measured by a semi-quantitative reaction and of the genin by the bulk volume measured (see next chart note[1]). The twelve previous procedures with the introduction of the zymogenic mediating agent, as the catalytic alternating systems, as those used in the examples 5, 6 and 7 is compared against the same four stages procedures that use alone the kernel's bearing related glycosidic substrate of the referred "sapote", without the use of biological external (exogenous) catalytic alternating systems of "emulsins" (exogenous glucosidases systems) to the ones presents in the powdered stages in test of the *Calocarpum*. The results are summarized in the following chart.

state kernels that obtained few genin and they didn't obtain sapogenins to the same last conditions, in the first column.

The application to the enzymatic substrate of the "degreased flour" (with solvent), that didn't obtain any yield in genin and in sapogenins, with the procedure without the use of an enzymatic alternating, external catalytic system, is contrasted against the use of these enzymatic alternating, exogenous, external zymogenic systems that gives high yields in sapogenins and in genin, when they are restored with these systems of another vegetable adequate, adapted, and peculiar, exogenous source, as with the systems of the examples 5, 6 and 7 of this application. The same as for the other states (stages) of the used kernels that give high yields in sapogenins and in genin when an enzymatic alternating, exogenous, external systems are used, that gives high yields.

Chart of results[1] of genin and sapogenins obtaining by zymogenic exogenous extrageneric vegetable ferments "emulsins", expressed in relative proportion for 1 Kg. of vegetable (powdered) matter. The marks indicate (−) smaller quantity and (+) bigger relative quantity.

| Pulverized | Without added Zymogen. | | With added zymogen as of the example 5. | | With added zymogen as of the example 6. | | With Added zymogen. as of the example 7 | |
|---|---|---|---|---|---|---|---|---|
| | Genin | -Sapogen. | Genin | -Sapogen. | Genin | -Sapogen. | Genin | -Sapogen. |
| Fresh. | − | −− | ++ | ++ | +++ | +++ | +++ | +++ |
| Dry. | −− | −−− | ++ | ++ | ++ | ++ | +++ | +++ |
| Degres. Flour | −−− | −−− | ++ | ++ | ++ | ++ | +++ | +++ |
| Exp. Crackling. | −−− | −−− | ++ | ++ | ++ | ++ | +++ | +++ |

[1]for the genin are practiced liquid: liquid extraction and they are quantified by volume (see example 4 of this application). The results for the sapogenins are obtained by semi-quantitative techniques of the soluble watery mixture that separates from the genin, an aliquot of the extract is taken and an excess of phenyl hydrazine hydrochloride dissolved in aqueous sodium acetate is used (ref. 14, procedure 12.9.1f) and it is compared against the standard prepared in a similar way prepared, using a sample of water.

Of the analysis of the results it is noticed that the procedure that obtained less result in the sapogenins and genin yielding, and that are used as a standard group medium (stage of kernels of the related "sapote"), against the other compared group procedures in test, is the one that does not use external (exogenous) zymogenic agents (first column). Inside this group the one that had smaller yield was the procedure that uses the degreased (without the employment of catalytic alternating systems as the added zymogenic described in the example 5, 6 and of this application) attributable to the smaller biological catalytic power of the kernels in this, degreased stages. This smaller yield situation is concluded because the achievement of this degreased by the use of organic solvent (mainly not polar solvent or of intermediate polarity for the flour obtaining, extracts the fats and different biochemical constituent denaturalizing the activity of the own biological catalysts characteristic of *Calocarpum* of the related species in test (and genus, *Chrysophyllum* or *Lucuma*); there is less yield in the obtaining in sapogenins and genin the same as for the "expression crackling", ascribed results to the employment conditions, in null utility obtaining in the yield of the "expression crackling", attributable to the use of heat, 80-110° C., that also denaturalize the enzymes characteristic of *Calocarpum*, in the demonstrations of the previous tests. Comparing the two last procedures, which already contains scarce enzymatic activity, for the explained "denaturalization" reasons of the own endogenous catalytic activity of the kernels in this way prepared, contrary to the powdered fresh state kernels that was the one that obtained more yields at these conditions (without the alternating, exogenous catalytic systems employment); continued by the dry Of the practiced procedures results to the vegetable matters of *Calocarpum*, in fresh, in dry, in the "degreased flour", and in form of "expression crackling" states (stages), the one which obtained the more yields with the addition of a external catalytic systems employment, is by means of the use of the substrates of the kernels in fresh state (as having applied in the procedures of the examples 5, 6 and 7), attributable to the external enzymatic addition and the own catalytic advantage power of the kernels in fresh conditions the reinforcement of this activity in the mediating transformations, by the employment of a biological alternating second catalytic system of another vegetable of different species, appropriate and peculiar that increases and accelerates the transformation at a time toward the sapogenins and genin.

When there is no an alternating exogenous, extrageneric catalytic system, there is a smaller transformation toward the sapogenins (and genin), this is for not having enough enzymatic catalytic transformation activity to the sapogenins (by this product detection mean).

It is concludes that the genus *Calocarpum* (and of the other genus and related species) do not contain these active catalytic (or not functional) systems. It is recognized that these transformations are practiced artificially achieved by unspecific as or specify exogenous enzymes systems (of peculiar glucosidasas) toward the related glycosides culminating in the sapogenins, reaction which lean to these two groups of substances, one acid and another amidic and soluble, as well as to the other expected genin extract product, oleaginous, aromatized and aldehydic compound.

The results of the yields in genin and in sapogenins of the other procedures in dry state or as "degreased flour" and as "expression crackling" states are not of underestimation with the employment of an alternating catalytic system of another species, as the employees in the examples 5, 6 or 7. It is noticed that with the employment of 1 kg of the "degreased flour" are almost the double of the substrate used compared with the un-degreased kernels (content of fixed lipids near 50%), methods which are also as convenient results in the yield for the sapogenins and genin by these obtaining means, of the employment of catalytic zimogénicos, biological alternating, exogenous system as those described in the example 5, 6 and 7.

EXAMPLE 9

Test for the Percutaneous Activity of the Sapogenins of *Calocarpum* (*Chrysophyllum* or *Lucuma*)

These cream to be verified uses in that demonstration the sapogenins (and genin) of the "sapotes" in a cosmetic and pharmaceutical preparation for their synergistic activity with the fixed total lipids or with some fraction of these oleaginous portion also of the "sapotes", that are so reason of the last referred preceding application of related patent, by means of the efficiency of the activity of this cream for the action of percutaneous absorption as an emulsion oils in water that on the whole it contains the sapogenins of *Calocarpum* main presumed responsible agent of the percutaneous activity and as adjuvant for this action the fixed lipids and to the genin of *Calocarpum*, (*Chrysophyllum* or *Lucuma*) in a cosmetic preparation. All the ingredients of *Calocarpum*, (*Chrysophyllum* or *Lucuma*) are according to the two related inventions of the "sapotes". The anionic emulsifying and moistening agents also cooperate in the mentioned activity contained in this cream.

The cream is wanted to be checked for their efficiency as percutaneous absorption vehicle of the hydroquinone to 0.8%, against the same cream but without sapogenins mixture. The hydroquinone is used to return the pigmentation to affected people of "lentigo spots" and macular skin stains senescence that requires to be absorbed by the "stratum corneum" and to pass to deep layers of the epidermis to exercise its effects. The treatment is not given alone for the problem of the stains but because skin care treatments are also concomitantly required.

The test is taken place in 4 women and 1 man from 28 to 49 years of age, which have the problem in the skin of the face due to hyper-pigmentation stains or commonly calls "paño" spots.

The products are applied subsequently every day by 28 days, in the affected region, applying from ½ to 1 tea spoonful, levels that correspond from approximately 0.3 to 0.5 g of the cream in test.

A lady and the gentleman in test receives the product #1, consisting of the vehicle of absorption and the hydroquinone, preparation of the example 11 of the related application of previously mentioned patent that contains the sapogenins mixture and the fixed total lipids as being used in the presiding exemplification, for their synergistic action that comprise any form of mixtures of these, of those that can embrace hydrated lipidic lamellar phases according to the two invention of the "sapotes". Two of the remaining ladies received the product #2, consisting on the same cream but removed of the main presumed responsible ingredient of the percutaneous activity, the sapogenins of *Calocarpum*. The fourth lady received so alone the percutaneous excipient, the same cream but without the pigmentation agent of the hydroquinone.

The results obtained at the end of the period of test for the individuals receiving the test product #1, that is the cream for treatment of the cutaneous senescence, as that of the example 11 of the related patent application, with the sapogenins of the *Calocarpum* of the example 7 in these application, were of the dissipation of the hyper pigmentation stains, "paño spots" more deeply and more quickly. The individuals that received the product #2, in the test, were not as efficient with the dissipations of the stains, or were skin cleared as so, as with the product #1. The two test groups were compared against the lady used as test control, that only received the percutaneous excipient as the cream but removed of the hydroquinone of the example 11 of the related presiding application, mentioned previously, as effectiveness control.

EXAMPLE 10

Demonstration of the Bacteriostatic Activity of the Sapogenins of *Calocarpum* (*Chrysophyllum* or *Lucuma*)

The test is based on the bacteriostatic power of the sapogenins to concentrations of 0.5 g/l, test that is carried out "in vitro" with 100 microlítros in a diffusion test with disks that contain the substance in test, applied in an agar plate, which are seeded with a standardized suspension of microorganisms. After the incubation for one night, the diameters of the inhibition areas or clearing around the disks are measured.

The results of the diffusion tests in agar "in vitro" over the susceptibility joined to other experiments demonstrate a high efficiency of the test as sapogenins extractive vegetable matter of "aglyconic" enzymatic hydrolyzate, as obtained of the example 7, to exercise germicidal effects. The inhibition areas were obtained for the mixture of sapogenins of 2.0 mm of diameter subsequent to the incubation. After the period of incubation in a cultivation medium with mixed axillary's cultivations, the inhibition area was of 1.5 mm of diameter that was in the same conditions. A liquid medium of cultivation also demonstrated that so single 500 mg of the dry extract in raw of "aglyconic" enzymatic hydrolyzate of sapogenins of *Calocarpum*, of the example 7, in 1 kg of substrate were enough to exercise germicidal power for all the germs inoculated in the development substrate, previously seeded. The same results were obtained with so single 300 mg of the acid isolated of the mixture of sapogenins of the example 6 that were added to a similar medium.

EXAMPLE 11

Test for the Genin of *Calocarpum, Chrysophyllum* or *Lucuma* as Rubefacient Agent with Activity in the Renovation of the Epidermis It is wanted to evaluate the genin of *Calocarpum*, (*Chrysophyllum* or *Lucuma*) as obtained of the example 6 according to this invention, as capillary rubefacient agent for which six affected gentlemen of premature alopecia are tried, to which are requested to subject themselves to one weeks of test, which consists on being applied from 0.5 to 1 ml of the diluted products in test in the affected area of the head scalp in the clean skin. The two men of the group #1, receives the mixture of genin of *Calocarpum*, in a preparation consisting on the product as obtained of the example 6, to 0.5% in an excipient. The excipient composition for 100 g is: water 20 g, propylenglycol 25 g, sunflower oil 54.5 g. The two men of the group #2, receives the same composition of the previous excipient and resorcinol to 0.5%. The two men of the group #3, receives the before mentioned excipient alone. The following questionnaire is registered and the pertinent observations of the test are made.

Age; sex; since when they present the alopecia; duration of the applied treatment;

1.—Was the treatment irritating: a) it was not irritating, b) light, c) moderate, d) high, e) severe.
2.—Irritation type: a) hyperaemia (heat), b) inflammation, c) vesication (it produces blisters)
3.—keratolytic (desquamation production): a) without effect, b) light, c) moderate, d) extensive.
4.—Scent: a) pleasant, b) without comment, c) unpleasant.
5.—Sensation when applying the products in test: a) pleasant, b) without comments, c) unpleasant.
6.—Comments of the test. Primary effects that the treated individual perceives: a) great benefit, b) helpful, c) without effect, d) harmful.
7.—Type of effects and observations.

The study gave as a result that the genin of *Calocarpum*, is effective as rubefacients for the region of the hairy scalp of the head producing moderate hyperaemia, more delicate than the resorcinol that is a capillary grateful rubefacient that also produces moderate keratolysis, in counter position with the effect of the genin of *Calocarpum* that do not produce it. The genin besides presents a pleasant aroma according to the survey.

It is concluded that the genin of *Calocarpum* have effects in the epidermal renovation, opening the cutaneous pore, taken place by the hyperaemia effect, allowing a greater circulation through the epidermis produced by these active ingredients.

EXAMPLE 12

Test for the Activity of the Sapogenins of *Calocarpum*, (*Chrysophyllum* or *Lucuma*) Over the Growth of the Lashes The test is based on a study in the activity of the products according to the invention in a period of time of test determined in the growth of the lashes, of women from 18 to 40 years of age, which manifest diminished growth, to those that are requested to apply the product on the lashes of the right eye with the well closed lid of the rehearse eye, with a small atomizer and to use the lashes of the left eye as control without receiving any trial product.

The products in test are applied subsequently during 42 days of duration of the test, without application the seventh day of the seven weeks of application, to a dose that is from 500 to 100 µl.

The study is made in 8 individuals divided in two groups of four individuals each one. The first group received preparations containing 0.5% of the product of the example 5, mixture of sapogenins of kernels of *Calocarpum*, in an excipient. The composition of the excipient for 100 g is 99.5 g of injectable water. The second group received alone the excipient.

The results of the study were obtained as average values at the end of the time of the test.

The analyzed values represented the development of the tried lashes against that of those not tried to the final period of the treatment using the lash of the left eye of the individuals tried as first internal control. The first group is compared against the second control group that received the excipient so alone in the right eye and without treatment in the left eye.

It is observed of the obtained data that the examined numbers of lashes in development state is increased much quicker in the group receiving the mixture of sapogenins of *Calocarpum*, according to the invention that in the group receiving the excipient, against the lash of the own left eye of all the individuals as internal first control in the test. It can be notice that given the cycle of growth of the lashes, it is possible to continue with the phase of growth of the lashes by means of the application for more prolonged periods of treatments.

It is deduced from the previous observations that the duration of the phase of growth of the lashes can be prolonged significantly and to stimulate the lashes in its growth and in its continuous renovation with the mixtures of sapogenins of *Calocarpum*, in a dose as that of this example without exercising secondary marked effects.

EXAMPLE 13

Gel for the Regulation of Greasy Skin 0.5 of the sapogenins of *Calocarpum*, (*Chrysophyllum* or *Lucuma*) as obtained in the example 7, are dissolved in 50.0 of water, later the solution is gelled by the addition of 49.5 of carbomer 940 to 3%.

The gel is applied daily by a period of 3 months stabilizing treatment of in the skin.

EXAMPLE 14

Gel for the Growth of the Lashes

Prepare the following compositions:

| Composition A: | |
|---|---|
| Sapogenins of *Calocarpum*, (*Chrysophyllum* or *Lucuma*) as obtained of the example 7. | 0.4 |
| Propylenglycol | 5.0 |
| Distilled water | 82.6 |
| Composition B: | |
| 1.25% carbopol 936 gel | 12.0 |

All the components of the composition A, first are mixed in the water, and the anhydrous carbopol 936 is introduced to give a gel that can be use once or twice a day to promote the growth of the lashes. In this preparation, the sapogenins are used as capillary stimulant of development and as antimicrobial conservative agents of the cosmetic preparation.

EXAMPLE 15

Treatment Rimel for the Promotion of Lashes Growth

In this example the fixed total lipids together with the sapogenins both of *Calocarpum* (*Chrysophyllum* or *Lucuma*), are included because of its synergistic effect in the development stimulation of the hair. These are prepared in the following composition:

| | |
|---|---|
| Sapogenins of *Calocarpum*, (*Chrysophyllum* or *Lucuma*) as obtained in the example 7. | 0.5 |
| Fixed total lipids of *Calocarpum*, (*Chrysophyllum* or *Lucuma*) | 10.8 |
| Carnauba wax | 5.0 |
| Bees wax | 15.0 |
| Isopropyl myristate | 10.0 |
| Stearic acid | 10.0 |
| Glyceril monostearete | 10.0 |

-continued

| | |
|---|---|
| Trietanolamine | 5.0 |
| Distilled water | 27.5 |
| Sodium alginate | 2.0 |
| Iron black oxidize | 5.0 |

EXAMPLE 16

Shampoo to Combat the Fall of the Hair, with Genin and Sapogenins of *Calocarpum* (*Chrysophyllum* or *Lucuma*)

| | |
|---|---|
| Sapogenins of *Calocarpum*, (*Chrysophyllum* or *Lucuma*) as obtained in the example 7. | 0.8 |
| Sodium laurylsulfate | 35.0 |
| Laurylsulfate monoethanolamine | 20.0 |
| Coconut diethanolamine | 2.1 |
| Citric acid | 1.3 |
| Sodium chloride | 0.3 |
| Genin of *Calocarpum* (*Chrysophyllum* or *Lucuma*), as obtained in the example 5. | 0.5 |
| Distilled water | 40.0 |

In this preparation, the sapogenins are used as capillary development stimulant agent and as antimicrobial preservative of the cosmetic preparation.

EXAMPLE 17

Epidermal Anti-Aging Liposomal Gel

The use of this gel is as prepared according to the example 14, except that the distilled water in the preparation of the gel is replaced with a watery solution containing 0.4% of sapogenins of *Calocarpum*, (*Chrysophyllum* or *Lucuma*) as obtained in the example 7.

The gel is applied in the skin, renovating and reforming where it is necessary to reduce the deterioration of the skin.

EXAMPLE 18

Fashionable Gel, to Combat Hair Lost

| | |
|---|---|
| Sapogenins of *Calocarpum* (*Chrysophyllum* or *Lucuma*), as obtained in the example 5. | 0.5 |
| 1.5% gel of Carbomer 940 | 50.0 |
| Collagen | 0.2 |
| Keratin hydrolyzate | 0.1 |
| Distilled water | 49.2 |

REFERENCES

1.—Document U.S. Pat. No. 4,139,619 (1979) 6-Amino-4-(substituted amino)-1,2-dihydro-1-hydroxy-2-iminopyriminie, Topical Compositions and Process for Hair Growth.
2.—Document U.S. Pat. No. 5,723,149 (1998) Use of Medicago Saponins for the Preparation of Cosmetic or Pharmaceutical Compositions, Especially Dermatological Compositions, Promoting Renewal of the Epidermis, Stimulating Hair Regrowth or Delaying Hair Loss.
3.—REMINGTON Farmacia; Gennaro A. R. editor, 19ª ed. Tomo 1 y 2; *Editorial Medica Panamericana*, (1995) p. 2418, 561, 562, 558 y 559.
4.—Morton, J.; Sapote, Canistel, Lucmo, Star Apple. In: Fruits of Warm. Climates, (1987) p. 397-410. http://newcrop.hort.purdue.edu/newcrop/morton/sapote_ars.html
5.—Pouteria sapote. Pouteria sapote Acc. 199800087 URL: http://florawww.eeb.uconn.edu/PalmWeb/199800087.html
6.—Bachstez, M., Santisteban Prieto, E. y Canales Gaja, A. M.; Estudios de la Lucumin, Glucósido Cianogéntico del Mamey (*lucuma mammosa* G.); *Ciencia* (*México*), 9, 200-202(1948).
7.—"Free Book", anonymous author; Lost Crops of the Incas Little-Known Plants of the Andes With Promise for World-wide Cultivation; *National Academy Press*, p. 263-266 (1989). http://books.nap.edu/books/030904264x/html/
8.—Morera, J. A.; Sapote (Pouteria sapote). En: Neglected Crops: 1492 from a different perspective. Bermejo, J. E. H. y León, J. (eds.); *Plant Production Protection Series* No 26 *FAQ*, Rome, Italy. (1994) p. 103-107.
9.—The Household Cyclopedia-Distillation p. 15, 16, 19. http://www.cairs.net.au/?sharefin/Cyclopedia/distilation.html
10.—Lambert, M. y Crane, J. H.; Tropical fruits. In: Advances in New Crops; Timber Press, Portland, Ed. J. Janick and J. E. Simon (1990) p. 337-355.
11.—Vetter, J., Plant Cyanogenic Glycosides. Toxicon, Pergamino, 38, 11-36 (2000). www.elsevier.com/locate/toxicon
12.—Haisman, D. R., Knight, D. J. Enzymic Hydrolysis Studies of Amygdalin; *Biochem. J.,* 103, 528-534(1967).
13.—Herbert, V., Laetrile: The Cult of Cyanide Promoting Poison for Profit; *Am. J. Clin. Nutr.,* 32, 112-1158 (1979).
14.—Pasto, D. J., Johnson, C. R.; Part I. Physical Methods of Separation, Purification, and Characterization: Separation and Purification. Part III. Identification of Organic Compounds: Qualitative and Quantitative Elemental Analyses, Functional Group Classification and Characterization In: Organic Structure Determination. Prentice-Hall, Inc., Englewood Cliffs, N.J. (1969)
15.—Takeda, T., Gonda, R., Hatano, K.; Constitution of Lucumin and its Related Glycosides from *Calocarpum sapota* Merrill; *Chemical and Pharmaceutical Bulletin*, Tokyo, 45(4), 697-699(1997).
16.—Document U.S. Pat. No. 6,124,362 (2000) Method for Regulating Hair Growth.
17.—Winholz, M.; The Merck Index $10^{th}$ ed., Rahway, N.J.: Merck and Co., Inc. (1983), p. 87, Monography no 620, Amygdalin.
18.—Merfort, I.; Phytochemical Study of *Lucuma mammosa; Fitoterapia*, 55(4), 316-317(1984).
19.—Willuhn, G., Merfort, I., Matthiesen, U.; The Occurrence of Lanosterol and 24-Methylenelanost-8-en-3β-ol in Leaves of *Symphoricarpus albus. Phytochemistry* 22(1) 137-141(1983).
20.—Allen Ph.; Poisonous and Injurious Plants of Panama. *America Journal of Tropical Medicine,* 23(suppl.), 3-76 (1943).
21.—Moertel et al.; A Pharmacological Study of Amygdalin. *J. Am. Assoc.,* 245(6), 591-594(1981).
22.—Winholz, M.; The Merck Index $10^{th}$ ed.; Rahway, N.J.: Merck and Co., Inc. (1983), p. 149, Monography no 1054, Benzaldehyde.
23.—Bradbury, J. H., Egan, S. V., Lynch, M. J.; Analysis of Cyanide in Cassava Using Acid Hydrolysis of Cyanogenic Glycosides. *Journal of Science and Food Agriculture,* 55, 277-290(1991).

24.—Gilchrist, D. C., Lueschen, W. E., Hittle, C. N.; Revised Method for the Preparation of Standards in the Sodium Picrate Assay of HCN. *Crop Science,* 7, 267-288 (1967).

25.—Amarowics, R., Shahidi, F.; Application of Sephadex LH-20 Chromatography for the Separation of Cyanogenic Glycosides and Hydrophilic Phenolic Fraction from Flaxseed. *Journal of Liquid Chromatography,* 17, 1291-1299 (1994).

26.—Winholz, M.; The Merck Index 10$^{th}$ ed., Rahway, N.J.: Merck and Co., Inc. (1983), p. 1115, Monography no 7648, Primaverosa.

27.—Budzikiewicz, H., Wilson, J. M., Djerassi C.; Mass Spectroscopy in Structural and Stereochemical Problems. XXXII. Pentacyclic Triterpenes. *J. Am. Chem. Soc.* 85, 3688-3699(1963).

28.—Vogel's; III, P, 172 Substituted Aliphatic Carboxylic Acids and their Derivatives. En: Textbook of Practical Organic Chemistry (4$^a$ ed.); Longman, London and New York; (1978) p. 534.

29.—Fieser, L. F. En: Organic Experiments. (3$^a$ ed.) Heath, Boston; (1964) p. 109.

30.—Gilman H.; Mandelic Acid. In: Org. Syn. coll. vol. I, 336 (1941). Org. Syn. coll. vol. III, 538 (1955); John Wiley & Sons, Inc.

31.—Winholz, M.; The Merck Index; 10$^{th}$ ed., Rahway, N.J.: Merck and Co., Inc. (1983), p. 816, Monography no 5539, Mandelic Acid.

32.—Petruccioli, M., Brimer, L. et al.; Production and Properties of Linamarase and Amygdalase Activities of *Penicillium auratiogriseum P35. Bioscience, Biotechnology and Biochemistry,* 63 (5), 805-812(1999).

33.—Document U.S. Pat. No. 4,621,023 (1986) Method of Homogenizing dispersions of Hydrated Lipidic Lamellar Phases and Suspensions Obtained by the Said Method.

34.—Document U.S. Pat. No. 4,508,703 (1985) Production of Pulverulent Mixtures of Lipidic and Hydrophobic Constituents.

35.—Eyjolfsson, R.; Constitution and Stereochemistry of Lucumin, a Cyanogenic Glycoside from *Lucuma mammosa* Gaertn. *Acta Chem. Scand.,* 25, 1898-1900(1971).

36.—Turczan, J. M., Medwick, T.; Qualitative and Quantitative Analysis of Amygdalin Using NMR Spectroscopy. *Analytical Letters,* 10, (7&8), 581-590(1977).

37.—Turczan, J, M., Medwick, T., Plank, W. M.; 220 MHz Nuclear Magnetic Resonance Studies of Amygdalin and Some Related Compounds. *J. Assoc. Off. Anal. Chem.,* 61, N°. 1, 192-207(1978).

38.—Turczan, J, M., Medwick, T.; Nuclear Magnetic Resonance Studies of Cyanogenetic Glycosides. *J. Assoc. Off. Anal. Chem.,* 62, No 1, 190-196(1979).

39.—Viehoever, A. y Mack, H.; Biochemistry of Amygdalin; *Am. Jour. Pharm.,* 107, 397-450(1935).

40.—Kakes, P.; Properties and Functions of the Cyanogenic System in Higher Plants. *Euphytica,* 48, 25-43(1990).

41.—Esen, A.; β-Glucosidase: Overview. En: β-Glucosidases, Biochemistry and Molecular Biology, ed. Esen, A., ACS Symposium Series 533; *American Chemical Society*, Washington, p. 1-14(1993).

42.—Poulton, J. E.; Enzymology of Cyanogenesis in Rosaceous Stones Fruit. In: β-Glucosidases, Biochemistry and Molecular Biology, ed. Esen, A., ACS Symposium Series 533, *American Chemical Society*, Washington, p. 170-190 (1993).

43.—Association of Official Agricultural Chemists. In: AOAC Official Methods of Analysis, 10$^{th}$ ed. (1965), p 341.

44.—Brimer, L., Tuncel, G., Nout, M. J. R.; Simple Screening Procedure for Microorganisms to Degrade Amygdalin. *Biotechnol. Techn.,* 7,683-687(1993).

45.—Brimer, L., Cicalini, A. R., Federici, F., Petruccioli, M.; Production of Beta-Glycosidases (Linamarase and Amygdalase) and Pectolytic Enzymes by *Penicillium* spp.; *World J. Microbiol. Biotechnol.,* 10, 203-206(1994).

46.—Brimer, L., Christensen, S. B., Molgaard, P., Nartey, F.; Determination of Cyanogenic Compounds by Thin-Layer Chromatography. I. A Desitometric Method for Quantification of Cyanogenic Glycosides, Employing Enzyme Preparations (β-Glucuronidase) from *Helix pomatia* and Picrate-Impregnated Ion-Exchange Sheets. *J. Agric. Food Chem.,* 31, 789-793(1983).

47.—Bradford, M.; A Rapid and Sensitive Method for Microgram Quantification of Protein Utilizing the Principle of Protein Dye Binding. *Anal. Biochem.,* 72, 248-254(1976).

48.—Fan, T. W. M., Conn, E. E.; Isolation and Characterization of Two Cyanogenic β-Glucosidases from Flax Kernels. *Arch. Bichem. Biophys.,* 243, 361-373(1985).

49.—Funaguma, T., Hara, A.; Purification of Two β-Glucosidases from *P. herquei* Banier and Sartoro, *Agric. Biol. Chem.,* 52, 749-755(1988).

50.—Hidalgo, M., Steiner, J., Eyzaguirre, J.; β-Glucosidase from *Penicillium purpurogenum*: Purification and Properties. *Biotechnol. Appl. Biochem.,* 15, 185-191(1992).

51.—Kuroki, G. W., Poulton J. E.; Comparison of Kernels Kinetic and Molecular Properties of Two Forms of Amygdalin Hydrolase from Black Cherry (*Prunus serotina* Ehrh.). *Arch. Biochem. Biophys.,* 247, 433-439(1986).

52.—Selmar, D., Lieberei, R., Biehl, B., Viogt, J.; Hevea Linamarase a Nonspecific β-Glycosidase. *Plant Physiol.,* 83, 557-563(1987).

53.—Yeoh, H. H., Wee, Y. C.; Some Properties of β-Glucosidases from Tropical Plant Species. *Phytochem.,* 35, 1391-1393(1994).

54.—Pocsi, I., Kiss, L, Hughes, M. A., Nanasi, P.; Kinetic Investigation of the Substrate Specificity of the Cyanogenic β-D-Glucosidase (Linamarase) of White Clover. *Arch. Biochem. Biophys.,* 272, 496-506(1989).

55.—Esser, A. J. A., Bosveld, M., Van der Grift, R. M., Voragen, A. G. J.; Studies on the Quantification of Specific Cyanogens in Cassava Products and Introduction of a New Chromogen. *J. Sci. Food Agric.,* 63, 287-296(1993).

56.—Seigler, D. S.; Isolation and Characterization of Natural Occurring Cyanogenic Compounds, *Phytochemistry,* 14, 9-29(1975).

57.—Epstein, J.; Estimation of Microquantities of Cyanide. *Anal. Chem.,* 19, 272-274(1947).

58.—Haskins, F. A., Gorz, H. J., Hill, R. M.; Colorimetric Determination of Cyanide in Enzyme-Hydrolyzed Extracts of dried Sorghum Leaves. *J. Agric. Food Chem.,* 36, 775-778(1988).

59.—Lambert, J. L., Ramasamy, J., Paukstelis, J. V.; Stable Reagent for the Colorimetric Determination of Cyanide by Modified König Reactions. *Anal. Chem.,* 47, 916-918 (1975).

60.—Rule, G. H., Harrower, J.; Optical Activity and the Polarity of Substituent Groups, Part 16. Application of the Thorpe-Ingold Valency Deflexion Hypothesis to Optically Active Compounds. *J. Chem. Soc.* p. 2319-2328(1930).

61.—Hara, S., Okabe, H. y Mihashi, K.; Gas-Liquid Chromatographic Separation of Aldose Enantiomers as Trimethylsilyl Ether of Methyl 2-(Polyhydroxyalkyl)-thiazolidine-4(R)-carboxilates. *Chem. Pharm. Bull.,* 35, 501-506 (1987).

62.—Mendoza, E. M. T., Kojima, M., Iwatsuki, N., Fukuba H. y Uritani, I.; Evaluation of some Methods for the Analysis of Cyanide in Cassava. En: Tropical Root Crops, Post-harvest Physiology and Processing; Eds Uritani I. & Reyes E. D. *Japan Scientific Societies Pres*, Tokyo, 235-242 (1984).

63.—Vetter, J., Haraszti, E.; Determination of Cyanoglycosides of Plant Tissue by the Modified Picric Acid Technique. *Agrokemia es Talajtan*, 24, 413-422(1975).

64.—Hughes, M. A., Esen, A.; Molecular Genetics of Plant Cyanogenic beta-Glucosidases. Beta-Glucosidases: Biochemistry and Molecular Biology. In: Symposium Patrocinated by the Division of the "Agricultural and Food Chemistry" in the 204$^a$ National Meeting of the "American Chemical Society", Washington DC, August 23-28(1992). *ACS Symposium Series,* 533,153-169(1993).

65.—Hickel, A., Hasslacher, M., Griengl, H.; Hydroxynitrile Lyases: Function and Properties. *Phisiologia Plantarum.* 98,891-898(1996).

66.—Klyne, W.; The Configuration of the Anomeric Carbon Atoms in some Cardiac Glycosides; *Biochem. J.,* 47, xli-xlii(1950).

67.—Itoh, T., Tamura, T., Iida T., Matsumoto T.; Gas Chromatographic Differentiation of 4-Desmethyl, 4-Monomethyl and 4,4-Dimethylsterols. *Steroids,* 23, (5) 687-694 (1974).

68.—De la Llata R. L.; Obtención de los Lípidos Fijos Totales de Semillas de la Familia Sapotácea para la Preparación de Cosméticos y Composiciones Farmacéuticas Dermatological, *Patent Appliance*, Mexico (July 2004) PCT/MX 2004/000051.

69.—Bondioli, P. et al.; Caratterizzazione Chimica del Seme di Zapote (*Lucuma mammosa*). *La Rivista Italiana delle Sostanze Grasse.* 73(5)229-230 (1996).

The invention claimed is:

1. A biochemical transformation process for obtaining the aglycones, genin plus sapogenins comprising of adding exogenous β-glycosidases enzymes, obtained from vegetable origin, other than from the family Sapotaceae and raw material for the transformation consisting of the coarse raw kernel, or a plurality of kernel products which contains the biochemical enzymatic substrates activity of the cyanoglycoside, the lucumin, plus the related glycosides, the lucuminic acid and the lucuminamide, that retain the activity of the original kernels as a biochemical method for yielding the genin plus of the sapogenins as enzymatic hydrolysis aglycones products wherein said raw material is obtained from particular species of the family Sapotaceae.

2. The process as claimed in claim 1, wherein the use of a kernel raw material for the transformation consists of the coarse raw kernel that retains the activity of the original kernels as a biochemical enzymatic substrates, which contains the cyanoglycoside and related glycosides, said kernel raw material is selected from the group consisting of:
a) Fresh or dry, whole, in pieces, milled or crushed coarse kernels;
b) A kernel solid residual product obtained by lipidic expression of kernels;
c) A kernel solid residual product obtained by lipid extraction of kernels or of the degreased flour of kernels;
d) A kernel product partially or completely degreased; and
e) Extract of glycosides selected from the group consisting of lucumin, lucuminic acid, lucuminamide, or the combination thereof.

3. The process as claimed in claim 2, wherein the kernel solid residual product obtained by lipidic expression of kernels, is acquired by subjecting raw fragmented kernels to mechanical expression, to the defined temperature from 80° C. to 110° C. and subsequently to the determined pressure of 38.30-81.40 Newton/meter' equivalent to 8-17 pounds/foot' and; leaving apart the obtained oleaginous liquid product, and recovering and using the solid residual product of the previous expression, as a kernel product for obtaining the genin and the sapogenins.

4. The process as claimed in claim 2, wherein the kernel solid residual product obtained by lipidic extraction of kernels or the product of degreased flour of kernels, is acquired by subjecting raw fragmented, milled, crushed or coarse grind kernels to extraction with a selected solvent of: methylene chloride, carbon tetrachloride, chloroform or dichloroethylene for approximately 24 hours; separating by filtrating and leaving apart the obtained oleaginous extracting liquid product, with solvents, that contains fixed lipids; and recovering the solid residual product of the previous extraction, wet with solvent, to dry it, crush it, and use it as the kernel product for obtaining the genin and the sapogenins.

5. The process as claimed in claim 2, where the kernel partially or completely degreased as a dried solid residual product, is obtained by subjecting raw fragmented, milled, crushed or coarse grind kernels to degreasing with non or medium polarity solvents, without the use of a polar solvent, to serve as substrate for the transformation into the aglycones, and use it as the kernel product for obtaining the genin and the sapogenins.

6. The process as claimed in claim 1, wherein the step of adding exogenous β-glycosidases enzymes to the coarse raw kernel or a plurality of kernel products or to the substrates directly, the cyanoglycoside and related glycosides of the particular species of the family Sapotaceae, further comprises: mixing otherwise one or several of the biochemical transformation kernel raw material as claimed in claim 2, in a watery solution and a suitable enzymatic preparation of exogenous β-glycosidases enzymes, at a pH from 3.0 to 7.0 with a temperature from 10 to 60° C., and for a period from 5 to 60 minutes or until a the reaction is completed to form a visible transforming mixture; separating the transforming mixture of the enzymatic must to a purified mixture of aglycones by boiling the mixture at a temperature from 80 to 110° C. for 15 to 180 minutes and separating the first boiling fraction of aromatic constituents formed consisting of a purified mixture of genin-sapogenins; subjecting of this fraction recovered of genin-sapogenins to liquid: liquid extraction to separate an oleaginous superior phase obtained, corresponding to the genin separation recovery and to separate a watery inferior phase corresponding to the sapogenins separation recovery, as obtained after this partition; subjecting the watery inferior phase, corresponding to the sapogenins separation water recovery to a liquid: liquid extraction with ethyl ether 1:1, or another water-immiscible solvent with similar polarity, to separate the organic fraction containing the sapogenins, and to subject the sapogenins recovery to evaporation to retire the solvent and to obtain a dry recovery of sapogenins; and perform a fractional crystallization of the acidic and amidic compounds of this dry recovery of sapogenins, by use of the crystallization solvents of, water, methanol, ethanol, or mixtures thereof, and obtain the isolated mandelic acid and isolated mandelamide of the last dry recovery of sapogenins; wherein producing the aglycones transformation result is to benzaldehyde, being the main constituent of the genin, besides, the transformation into mandelic acid and mandelamide respectively, as the main constituents of the sapogenins, as obtained after separation to the individual aglycones.

7. The process as claimed in claim 1, wherein the genin is obtained as a purified compound benzaldehyde.

8. The process as claimed in claim 1, wherein the sapogenins are obtained as purified compounds, mandelic acid and mandelamide.

9. The process as claimed in claim 1, wherein the genin are used in preparation of cosmetics and pharmaceutical topical compositions, to act as rubefacient, promoting opening of the pores, through epithelial penetration.

10. The process as claimed in claim 1, wherein the genin are used for flavoring or scenting foods and cosmetics.

11. The process as claimed in claim 1, wherein the sapogenins or the sapogenins constituents are used for preparation of cosmetics and pharmaceutical topical compositions, to act on skin like astringents and promote epithelial penetration.

12. The process as claimed in claim 1, wherein the sapogenins or the sapogenins constituents are used for preparation of cosmetics and pharmaceutical topical compositions to act as an exfoliate with positive effects in the renovation and stimulation of the skin.

13. The process as claimed in claim 1, wherein the sapogenins or the sapogenins constituents are used for preparation of cosmetics and pharmaceutical topical compositions, to act as a stimulant and as capillary promoter.

14. The process as claimed in claim 1, wherein the sapogenins or the sapogenins constituents are used for preparation of cosmetics and pharmaceutical topical compositions to act as a preservative with active bacteriostatic and fungistatic activities on topical compositions or in the skin.

15. The process as claimed in claim 1, wherein the raw material for the biochemical transformation process for obtaining the aglycones, genin plus sapogenins comprising of the use of coarse raw kernel, or a plurality of kernel products which contains the biochemical enzymatic substrates, is of the particular species of the family Sapotaceae selected from the particular species *Calocarpum sapota, Calocarpum mammosum, Calocarpum viride, Lucuma domingensis, Lucuma salicifolia, Lucuma obovata, Lucuma hypoglauca, Chrysophyllum mexicanum*, or *Chrysophyllum caimito*.

\* \* \* \* \*

UNITED STATES PATENT AND TRADEMARK OFFICE
CERTIFICATE OF CORRECTION

PATENT NO. : 9,017,736 B2  Page 1 of 1
APPLICATION NO. : 11/632961
DATED : April 28, 2015
INVENTOR(S) : Luis De La Llata Romero It is certified that error appears in the above-identified patent and that said Letters Patent is hereby corrected as shown below:

Title Page, item (54) and in the Specification, Column 1, line 5 in the title, the word "ÃŸ-GLYCOSIDASES" should read --β-GLYCOSIDASES--.

Signed and Sealed this
Eighteenth Day of August, 2015

Michelle K. Lee
*Director of the United States Patent and Trademark Office*